United States Patent [19]

Arimoto et al.

[11] Patent Number: 4,603,198

[45] Date of Patent: Jul. 29, 1986

[54] CEPHALOSPORIN DERIVATIVES

[75] Inventors: Masahiro Arimoto, Chiba; Hiroaki Tagawa, Tokyo; Minoru Furukawa, Chiba, all of Japan

[73] Assignee: Daiichi Seiyaku Co., Ltd., Tokyo, Japan

[21] Appl. No.: 482,734

[22] Filed: Apr. 6, 1983

[30] Foreign Application Priority Data

Apr. 6, 1982 [JP] Japan .................................. 57-57010
Jul. 29, 1982 [JP] Japan ................................ 57-132501
Nov. 4, 1982 [JP] Japan ................................ 57-193607

[51] Int. Cl.$^4$ .................. C07D 501/56; A61K 31/545
[52] U.S. Cl. ...................................... 544/25; 544/22; 544/27
[58] Field of Search ..................... 544/16, 21, 22, 25

[56] References Cited

U.S. PATENT DOCUMENTS 4,271,157 6/1981 Denzel et al. ........................ 544/25
4,399,131 8/1983 Durkheime et al. .................. 544/21

FOREIGN PATENT DOCUMENTS 54-132593 10/1979 Japan .
56-77287 6/1981 Japan .

Primary Examiner—Nicholas S. Rizzo
Attorney, Agent, or Firm—Sughrue, Mion, Zinn, Macpeak, and Seas

[57] ABSTRACT

Novel cephalosporin derivatives and physiologically acceptable salts thereof which are useful as antibacterial agents against gram-negative and gram-positive bacteria, and a process for preparing these compounds are disclosed.

1 Claim, No Drawings

CEPHALOSPORIN DERIVATIVES

FIELD OF THE INVENTION

This invention relates to novel cephalosporin derivatives which are useful as antibacterial agents.

BACKGROUND OF THE INVENTION

Japanese patent application (OPI) No. 77287/1981 describes 7β-(2-(2-aminothiazol-4-yl)-2-((1H-tetrazol-5-yl)methoxyimino)acetamido)-3-pyridiniomethyl-3-cephem-4-carboxylate and 7β-(2-(2-aminothiazol-4-yl)-2-((imidazol-2-yl)methoxyimino)acetamido)-3-pyridiniomethyl-3-cephem-4-carboxylate, Japanese patent application (OPI) No. 139523/1979 describes 7β-(2-(2-aminothiazol-4-yl)-2-((imidazol-1-yl)ethoxyimino)acetamido)-3-acetoxymethyl-3-cephem-4-carboxylic acid (the term "OPI" as used herein refers to a "published unexamind patent application").

DETAILED DESCRIPTION OF THE INVENTION

This invention relates to a novel antibacterial agent, and more particularly to cephalosporin derivatives of formula (I)

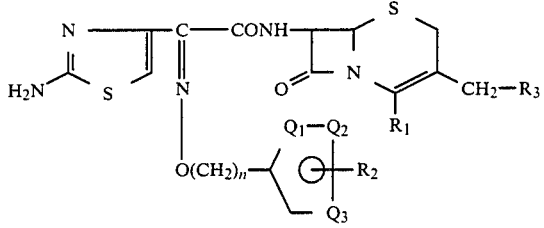

wherein
  $R_1$ represents COOH, COO⁻ or COOM, wherein M represents an alkali metal or an alkaline earth metal,
  $Q_1$, $Q_2$ and $Q_3$ each represents a nitrogen atom or a carbon atom and at least two of $Q_1$, $Q_2$ and $Q_3$ represent nitrogen atoms,
  $R_2$ represents a hydrogen atom or an alkyl group having from 1 to 6 carbon atoms,
  $R_3$ represents an acyloxyl group having from 2 to 7 carbon atoms,

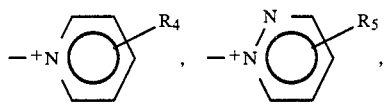

or —S—$R_6$,
  wherein $R_4$ and $R_5$ each represents a hydrogen atom, a carbamoyl group or an alkyl group having from 1 to 6 carbon atoms, $R_6$ represents a 5- or 6-membered ring which contains from 1 to 4 hetero atoms and may be substituted with an alkyl group having from 1 to 6 carbon atoms, n represents 1 or 2,
and physiologically acceptable salts thereof.

In the above formula (I), the group of the partial structure

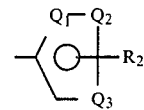

includes the following cyclic groups

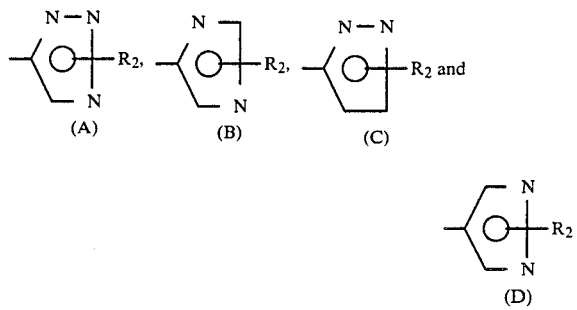

wherein $R_2$ is as defined above.

Examples of the 5- or 6-membered ring defined as $R_6$ include 1H-tetrazolyl, 2H-tetrazolyl, 1,2,3-triazolyl, 1,2,4-triazolyl, pyridyl, pyrimidinyl, pyridazinyl, pyrazolyl, thiazolyl, 1,2,3-thiadiazolyl, 1,2,4-thiadiazolyl, 1,3,4-oxadiazolyl and 1,2,5-oxadiazolyl.

The 2-aminothiazol-4-yl group of the compounds of formula (I) and their intermediates can exist in the form of two tautomers having the structure shown below, however, the group is structurally represented and named as 2-aminothiazol-4-yl group throughout the specification and claims and both forms (E) and (F) are within the scope of this invention.

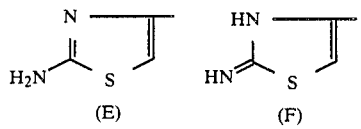

Since the compound of formula (I) has an oxyimino group in the structure, the compound can be obtained in the form of syn-isomer (G) or anti-isomer (H) or a mixture of these two forms.

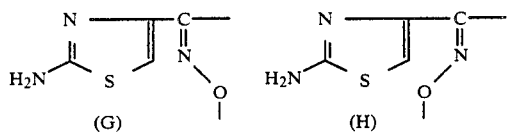

Apparently, either of them is within the scope of this invention, however, it is preferable to obtain the final product in the syn-form since syn-form has more excellent activity than anti-form does, in general.

The compounds of this invention can form acid addition salts thereof with an inorganic or organic acid such as hydrochloric acid, sulfuric acid, formic acid, maleic acid and the like.

The compounds of this invention have more excellent antibacterial activity against gram-negative and gram-positive bacteria, in particular against *Pseudomonas aeruginosa* in comparison with the known compounds described before.

The process for preparing the compound of formula (I) is illustrated as Scheme I.

Throughout this specification, symbols are used consistently to represent the kind of atoms, substituents, numbers and etc. as defined below.

$R_1$ represents COOH, COO⁻ or COOM, wherein M represents an alkali metal or an alkaline earth metal.

$R_2$ represents a hydrogen atom or an alkyl group having from 1 to 6 carbon atoms.

$R_3$ represents an acyloxyl group having from 2 to 7 carbon atoms,

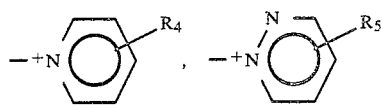

or —S—$R_6$.

$R_4$ and $R_5$ each represents a hydrogen atom, a carbamoyl group or an alkyl group having from 1 to 6 carbon atoms.

$R_6$ represents a 5- or 6-membered ring which contains from 1 to 4 hetero atoms and may be substituted with an alkyl group having from 1 to 6 carbon atoms.

$R_7$ represents the same as the definition of $R_1$ or COOR$_9$.

$R_8$ represents a hydrogen atom or a protecting group for amino group.

$R_9$ represents a protecting group for carboxyl group.

$Q_1$, $Q_2$ and $Q_3$ each represents a nitrogen atom or a carbon atom and at least two of $Q_1$, $Q_2$ and $Q_3$ represent nitrogen atoms.

$Q_{11}$ represents the same as the definition of $Q_1$ or a protected nitrogen atom.

$Q_{21}$ represents the same as the definition of $Q_2$ or a protected nitrogen atom.

$Q_{31}$ represents the same as the definition of $Q_3$ or a protected nitrogen atom.

n represents 1 or 2.

X represents a halogen atom or an acyloxyl group having from 2 to 7 carbon atoms.

Y represents a hydroxyl group or a halogen atom.

Scheme I

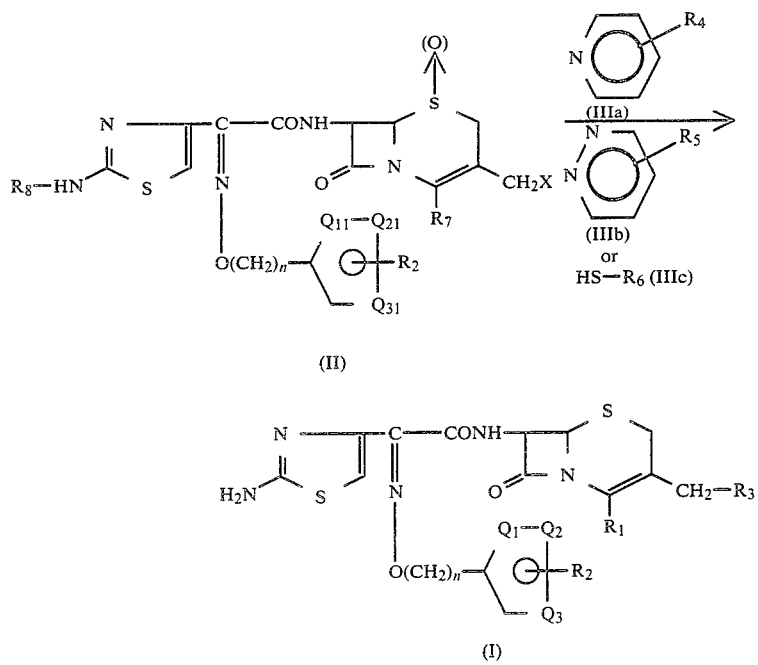

To describe the process of Scheme I more precisely, when X of formula (II) represents an acyloxyl group, the process comprises reacting a compound of formula (IIa)

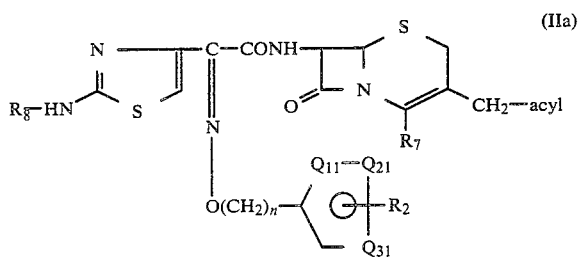

with a compound of formula (IIIa), (IIIb) or (IIIc) and then, optionally, eliminating the protecting group(s), ($R_7$, $R_8$, $Q_{11}$, $Q_{21}$, $Q_{31}$), and, when X represents a halogen atom, the process comprises reacting a compound of formula (IIb)

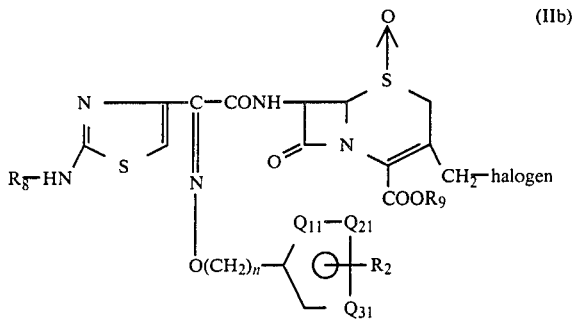

with a compound of formula (IIIa), (IIIb) or (IIIc) to produce a compound of formula (IV)

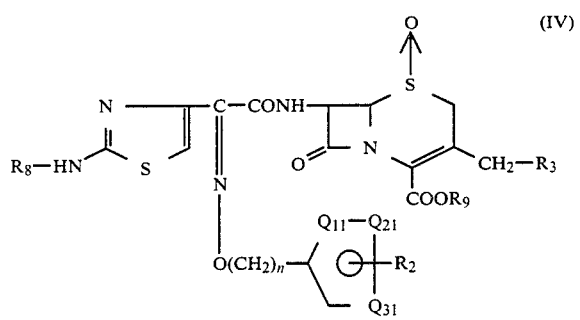

and converting the sulfoxide part of the compound of formula (IV) to sulfide and then, optionally, eliminating the protecting group(s) ($R_8$, $R_9$, $Q_{11}$, $Q_{21}$, $Q_{31}$).

The reaction of compound of formula (IIa) with the compound of formula (IIIa), (IIIb) or (IIIc) is performed in the presence of a suitable solvent such as water, acetone, ethyl methyl ketone, formamide, dimethylformamide, dimethylacetamide or a mixture thereof at 0°–120° C., preferably at 50°–90° C. It is preferred to perform the reaction in th presence of an aqueous solvent adjusted to pH 5–8 with an acid or a base. The reaction may be carried out in the presence of an alkali metal halide such as sodium iodide, potassium iodide, sodium bromide or potassium bromide, or a salt of thiocyanic acid such as potassium thiocyanate or sodium thiocyanate.

The reaction of the compound of formula (IIb) with the compound of formula (IIIa), (IIIb) or (IIIc) is performed in the absence of solvent or in the presence of a suitable organic solvent such as acetone, ethyl methyl ketone, chloroform, methylene chloride, tetrahydrofuran, dimethylformamide, dimethylacetamide or a mixture thereof at −50° to 100° C., conveniently at room temperature.

The compound of formula (IIa) or (IIb) and the compound of formula (IIIa), (IIIb) or (IIIc) are reacted theoretically in a molar ratio of about 1:1, but it is preferred to employ the compound of formula (IIIa), (IIIb) or (IIIc) in a slightly molar excess and usually, the compound of formula (IIIa), (IIIb) or (IIIc) is employed in 1 to 30 moles per mole of the compound of formula (IIa) and in 1 to 10 moles per moles of the compound of formula (IIb).

In the reaction for converting the sulfoxide part of the compound of formula (IV) to sulfide, the compound of formula (IV) is reacted with phosphorus trichloride or phosphorus tribromide in the presence of a suitable solvent such as dimethylformamide, dimethylacetamide, chloroform, methylene chloride or tetrahydrofuran. It is preferred to perform the reaction at −70° to 50° C. Phosphorus trichloride or phosphorus tribromide is usually employed in 1 to 10 moles per mole of the compound of formula (IV). Alternatively, the conversion can be performed by reacting the compound of formula (IV) with acetyl chloride to produce the corresponding acyloxysulfonium salt or the corresponding alkoxysulfonium salt and then reducing the resulting salt with sodium dithionite or with an iodide such as potassium iodide in the presence of a water miscible solvent such as acetic acid, acetone, tetrahydrofuran, dioxane, dimethylformamide or dimethylacetamide. It is preferred to perform the reductive reaction at −70° to 50° C.

The reaction for eliminating the protecting group for amino group and for carboxyl group is performed by a known reaction generally used in synthesis of peptides or β-lactam derivatives. That is, examples of the known reaction include a hydrolytic elimination of protecting group by an acid or a base and a reductive elimination of the protecting group.

The hydrolytic elimination by acid is favorable for eliminating the protecting group such as trityl group, formyl group or tertiary butoxycarbonyl group bonded to amino group and tertiary butyl group or p-methoxybenzyl group bonded to carboxyl group. Examples of the acid include an organic acid such as formic acid and trifluoroacetic acid, an inorganic acid such as hydrochloric acid and a mixture thereof. The reaction is carried out in the presence of a suitable solvent, for example, water, organic solvents such as dioxane, methylene chloride or tetrahydrofuran or a mixture thereof at a temperature of −70° to 50° C. The reaction may be carried out in the presence of a scavenger such as anisole or thioanisole.

The hydrolytic elimination by base is suitable for eliminating an acyl group such as trifluoroacetyl group bonded to amino group in the presence of a solvent such as a usual organic solvent, water or a mixture thereof at −20° to 50° C. Examples of the base include inorganic bases; alkali metal hydroxides such as sodium hydroxide; alkaline earth metal hydroxides such as calcium hydroxide and organic bases such as triethylamine.

The reductive elimination includes two types of reactions. The one reaction is performed by using a heavy metal such as zinc for elimination of a haloalkoxycarbonyl group such as trifluoroethoxycarbonyl group bonded to amino group and the other is performed by catalytic reduction for elimination of a p-nitrobenzyl group bonded to carboxyl group. These reactions are carried out in the presence of a solvent such as a usual organic solvent, water or a mixture thereof at room temperature, under cooling or under mild heating.

The compounds of formula (IIa) and (IIb) can be produced by acylating a compound of formula (V),

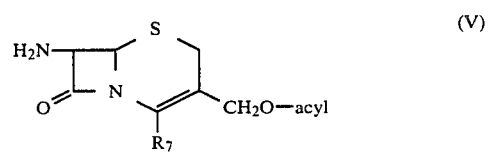

or a compound of formula (VI),

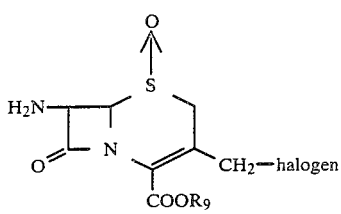

with a compound of formula (VII)

in the presence of a condensing agent such as dicyclohexylcarbodiimide or a mixture of dimethylformamide and phosphorus oxychloride, or with a reactive derivative of the compound of formula (VII). Examples of the reactive derivative are acid halide, preferably acid chloride, and active ester thereof such as the ester of the compound of formula (VII) with N-hydroxysuccinimide, N-hydroxyphthalimide or 1-hydroxybenzotriazole. The above acylation is usually carried out in a solvent such as methylene chloride, tetrahydrofuran, ethyl acetate and dimethylformamide. Then, optionally, the protecting group(s) ($R_8$, $R_9$, $Q_{11}$, $Q_{21}$, $Q_{31}$) of the resulting compounds is eliminated by the same reaction described before.

Alternatively, the compound of formula (I) can be produced from the compound of formula (VIII) as illustrated below.

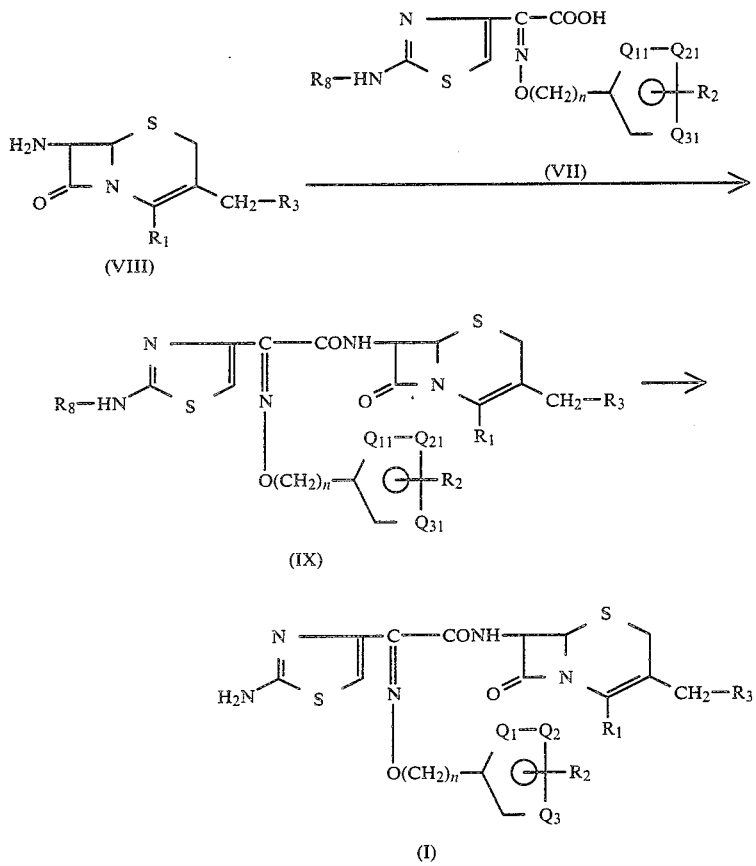

That is, the compound of formula (VIII) is acylated with the compound of formula (VII) or the reactive derivatives of the compound of formula (VII) using an analogous procedure to that described above to produce the compound of formula (IX). Then the protecting group for amino group of the compound of formula (IX) is eliminated by the same reaction described before to produce the compound of formula (I).

The compounds of formula (VII) can be prepared by the process outlined below.

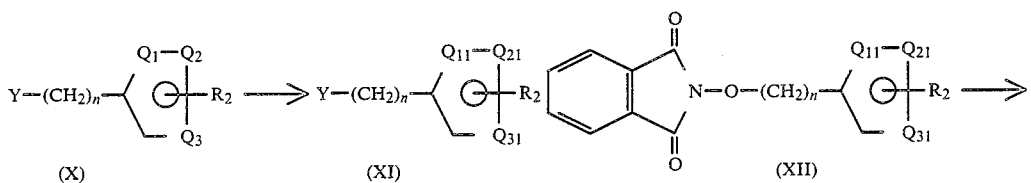

-continued $$\text{H}_2\text{N}-\text{O}-(\text{CH}_2)_n-\underset{Q_{31}}{\overset{Q_{11}-Q_{21}}{\underset{}{\bigoplus}}}-R_2 \quad \xrightarrow{R_8-\text{HN}\underset{S}{\overset{N\underset{}{\underset{}{\parallel}}\text{CO}-\text{COOH}}{\underset{}{\bigvee}}}} \quad R_8-\text{HN}\underset{S}{\overset{N\underset{N}{\underset{}{\parallel}}\text{C}-\text{COOH}}{\underset{}{\bigvee}}}\underset{}{\overset{}{\text{O}(\text{CH}_2)_n}}-\underset{Q_{31}}{\overset{Q_{11}-Q_{21}}{\underset{}{\bigoplus}}}-R_2$$

(XIII)          (XVI)          (VII)

That is, the compound (X) is converted to the compound (XI) by introducing a protecting group for amino group. When Y represents a halogen atom, the compound (XI) is treated with N-hydroxyphthalimide to produce the compound (XII) and when Y represents hydroxyl group the compound (XI) is treated with N-hydroxyphthalimide in the presence of triphenylphosphine and ethyl azodicarboxylate to produce the compound (XII). Alternatively, the compound (XII) can be produced by reacting the compound (X) with N-hydroxyphthalimide using the same procedures as described above and then introducing a protecting group for amino group. The compound (XII) is treated with hydrazine or hydrochloric acid to produce the compound (XIII). The compound (XIII) is treated with the compound (XIV) to produce the compound (VII).

The antibacterial activity (in vitro) of the preferred compounds of this invention are shown in the following Table 1 in comparison with known compounds having a structure similar to that of the compounds of this invention. All compounds of Table 1 are syn isomers.

SSB: Saturated aqueous solution of sodium bicarbonate
SSC: Saturated aqueous solution of sodium chloride
TLC: Thin layer chromatography
HPLC: High-performance liquid chromatography
Supports used in chromatography are as follows:
Bondapak: $\mu$ Bondapak $C_{18}$, a product of Waters Associates
Partisil: a product of Whatman Inc.
HP-20: Diaion HP-20, a product of Mitsubishi Chemical Industries Ltd.

As for IR data, only wave numbers are shown and those mean the value of $\nu_{max}^{KBr}$ cm$^{-1}$.

PRODUCTION OF STARTING MATERIAL

Referential Example 1

A mixture of ethanol and 270 mg of sodium was cooled in an ice-bath and 1.91 g of N-hydroxyphthalimide was added to the mixture. 594 mg of 4-(chloromethyl)imidazole hydrochloride was added thereto under stirring at room temperature and the resulting mixture

TABLE 1

| | Minimum Inhibitory Concentration (MIC, mcg/ml) ($10^6$/ml of bacteria were seeded) | | | | | | | | | | |
|---|---|---|---|---|---|---|---|---|---|---|---|
| | Known Compounds | | | Compounds of This Invention | | | | | | | |
| Test Organisms | a | b | c | IA | IB | IC | ID | IE | IF | IG | IH |
| E. coli, NIHJ | <0.1 | 0.10 | 0.20 | 0.10 | <0.1 | <0.1 | <0.1 | <0.1 | <0.1 | <0.1 | <0.1 |
| Pr. vulgaris, 08601 | <0.1 | 0.10 | 0.39 | 0.10 | 0.2 | 0.1 | <0.1 | 0.1 | 0.1 | 0.2 | <0.1 |
| Ser. marcescens, 10104 | 0.39 | 0.39 | 0.20 | 0.10 | 0.2 | 0.2 | 0.39 | 0.2 | 0.20 | 0.1 | 0.78 |
| Ps. aeruginosa, 32104 | 25.0 | 12.5 | 6.25 | 1.56 | 1.56 | 1.56 | 12.5 | 6.25 | 3.13 | 3.13 | 12.5 |
| Ps. aeruginosa, 32121 | 12.5 | 50.0 | 25.0 | 1.56 | 12.5 | 3.13 | 3.13 | 3.13 | 3.13 | 3.13 | 6.25 |
| S. aureus, 209p | 3.13 | 3.13 | 1.56 | 0.20 | 1.56 | 0.39 | 0.78 | 0.20 | 0.78 | 1.56 | 0.78 | a: Cephotaxim
b: 7β-(2-(2-aminothiazol-4-yl)-2-((1H—tetrazol-5-yl)methoxyimino)acetamido)-3-(1-pyridinio)methyl-3-cephem-4-carboxylate dihydrochloride
c: 7β-(2-(2-aminothiazol-4-yl)-2-((imidazol-2-yl)methoxyimino)acetamido)-3-(1-pyridinio)methyl-3-cephem-4-carboxylate
IA: 7β-(2-(2-aminothiazol-4-yl)-2-((imidazol-4-yl)methoxyimino)acetamido)-3-(1-pyridinio)methyl-3-cephem-4-carboxylate trihydrochloride
IB: 7β-(2-(2-aminothiazol-4-yl)-2-((imidazol-4-yl)methoxyimino)acetamido)-3-(4-carbamoyl-1-pyridinio)methyl-3-cephem-4-carboxylate trihydrochloride
IC: 7β-(2-(2-aminothiazol-4-yl)-2-((pyrazol-3-yl)methoxyimino)acetamido)-3-(1-pyridinio)methyl-3-cephem-4-carboxylate
ID: 7β-(2-(2-aminothiazol-4-yl)-2-((imidazol-4-yl)methoxyimino)acetamido)-3-(1-methyl-1H—tetrazol-5-yl)-3-cephem-4-carboxylic acid
IE: 7β-(2-(2-aminothiazol-4-yl)-2-((pyrazol-4-yl)methoxyimino)acetamido)-3-(1-pyridinio)methyl-3-cephem-4-carboxylate
IF: 7β-(2-(2-aminothiazol-4-yl)-2-((5-methylimidazol-4-yl)methoxyimino)acetamido)-3-(1-pyridinio)methyl-3-cephem-4-carboxylate
IG: 7β-(2-(2-aminothiazol-4-yl)-2-((imidazol-4-yl)methoxyimino)acetamido)-3-(4-methyl-1-pyridinio)methyl-3-cephem-4-carboxylate
IH: 7β-(2-(2-aminothiazol-4-yl)-2-((imidazol-4-yl)methoxyimino)acetamido)-3-acetoxymethyl-3-cephem-4-carboxylate As can be seen from Table 1, the compounds of this invention exhibit higher antibacterial activity than the known compounds.

With respect to toxicity of the compounds of this invention, the acute toxicity (LD$_{50}$) of the compound (IA) is more than 2.5 g/kg and that of the compound (IC) is more than 2 g/kg in mice (i.v.).

The present invention is further illustrated by the following Referential Examples and Examples. In these examples, "ether" means diethyl ether unless otherwise indicated and the following abbreviations were used.
DMF: N,N-Dimethylformamide
THF: Tetrahydrofuran
DCC: N,N'-Dicyclohexylcarbodiimide was stirred for 14 hours. The solvent was distilled off and SSB was added to the residue and the mixture was extracted with chloroform. The extract was washed with SSC and dried with sodium sulfate and then concentrated to dryness. The residue was recrystallized from a mixture of diisopropyl ether and ether to give 553 mg of N-((imidazol-4-yl)methoxy)phthalimide with mp 163°-165° C.

Analysis for $C_{12}H_9N_3O_3$: Calculated: C 59.26, H 3.73, N 17.28; Found: C 59.20, H 3.88, N 17.22

1.483 g of the above product was dissolved in 50 ml of chloroform and 1.651 g of trityl chloride was added thereto. 890 mg of triethylamine was added to the mixture under cooling in an ice-bath and the resulting mixture was stirred overnight at room temperature. The reaction mixture was washed with a diluted aqueous solution of sodium bicarbonate and SSC and dried with sodium sulfate and then concentrated to dryness. The residue was recrystallized from a mixture of ether and petroleum ether to give 2.1 g of N-((N-tritylimidazol-4-yl)methoxy)phthalimide with mp 155°–157° C.

Analysis for $C_{31}H_{23}N_3O_3$: Calculated: C 76.68, H 4.78, N 8.66; Found: C 76.81, H 4.90, N 8.50

9.57 g of the above product was suspended in 150 ml of ethanol and 0.99 g of hydrazine hydrate was added thereto. The resulting mixture was stirred for 14 hours at room temperature. The insoluble material precipitated was removed by filtration and the filtrate was concentrated to dryness. The residue was purified by silica gel column chromatography with 1% methanol-chloroform eluent and recrystallized from a mixture of ether and n-hexane to give 6.51 g of 4-aminooxymethyl-N-tritylimidazole with mp 138°–139° C.

Analysis for $C_{23}H_{21}N_3O$: Calculated: C 77.72, H 5.96, N 11.82; Found: C 77.74, H 5.97, N 11.74

IR: 1595, 1490, 1445

NMR (CDCl$_3$, δ, ppm): 4.63 (2H, s, —O—CH$_2$), 6.88 (1H, s, C$_5$—H of imidazole), 7.06–7.50 (m, trityl and imidazole)

3.50 g of the above product was dissolved in 200 ml of methanol and 3.39 g of (2-tritylaminoethiazol-4-yl)glyoxylic acid was added thereto. The resulting mixture was stirred for 12 hours at room temperature. The precipitate formed was collected by filtration and washed with methanol and ether to give 5.31 g of 2-(2-tritylaminothiazol-4-yl)-2-((N-tritylimidazol-4-yl)methoxyimino)acetic acid with mp 186°–188° C. (decomposition) as a white powder.

Analysis for $C_{47}H_{37}N_5O_3S$: Calculated: C 75.08, H 4.96, N 9.32; Found: C 74.84, H 5.17, N 9.35

IR: 1720

CW-NMR (DMSO-d$_6$, δ, ppm): 4.96 (2H, s, —O—CH$_2$—), 6.77 (1H, s, C$_5$—H of thiazole), 6.90–7,50 (m, trityl and imidazole)

Referential Example 2

7 g of N-hydroxyphthalimide was dissolved in 120 ml of DMF and then 9.8 g of potassium carbonate and 300 mg of 18-Crown-6(Merck & co, Ltd.) were added thereto. A mixture of 4.3 g of 4-(2-chloroethyl-)imidazole hydrochloride and 30 ml of DMF was added to the mixture under stirring. The resulting mixture was stirred for 15 hours at 50° C. After cooling, the insoluble material was removed by filtration and the filtrate was evaporated and then chloroform was added to the residue. The mixture was washed with SSB and SSC and dried with sodium sulfate and concentrated to dryness. The residue was washed with ether to give 2.9 g of N-(2-imidazol-4-yl)ethoxy)phthalimide with mp 145°–146° C. as a hygroscopic colorless powder.

Analysis for $C_{13}H_{11}N_3.H_2O$: Calculated: C 56.72, H 4.76, N 15.27; Found: C 56.40, H 4.83, N 15.16

IR: 1780, 1730

NMR (CDCl$_3$-DMSO d$_6$, δ, ppm): 2.98 (2H, t, J=9 Hz, —CH$_2$—C—), 4.37 (2H, t, J=9 Hz, —CH$_2$—O—), 6.95 (1H, s, C$_5$—H of imidazole), 7.51 (1H, s, C$_2$—H of imidazole), 7.86 (4H, s, phenyl)

725 mg of the above product was dissolved in 50 ml of chloroform and then 0.42 ml of triethylamine and 840 mg of trityl chloride were added thereto. The resulting mixture was stirred for 3 hours at room temperature. The reaction mixture was washed with an aqueous solution of sodium bicarbonate and SSC and dried with sodium sulfate and then concentrated to dryness. The residue was purified by silica gel column chromatography with chloroform eluent to give 1.28 g of N-(2-(N-tritylimidazol-4-yl)ethoxy)phthalimide with mp 177° C. as colorless granular crystals.

Analysis for $C_{32}H_{25}N_3O_3$: Calculated: C 76.93, H 5.04, N 8.41; Found: C 76.81, H 5.08, N 8.28

IR: 1780, 1725

NMR (CDCl$_3$, δ, ppm): 3.07 (2H, t, J=9 Hz, —CH$_2$—C—), 4.46 (2H, t, J=9 Hz, —CH$_2$—O—), 6.78 (1H, s, C$_5$—H of imidazole), 7.05–7.40 (16H, m, trityl, C$_2$—H of imidazole), 7.65–7.85 (4H, m, phenyl)

1.28 g of the above product was dissolved in 50 ml of methylene chloride and 133 mg of hydrazine hydrate was added thereto. The resulting mixture was stirred for one hour at room temperature. A 10% aqueous solution of sodium hydroxide was added to the reaction mixture in order to dissolve the insoluble material and the mixture was extracted with chloroform. The extract was washed with SSC and dried with sodum sulfate and then concentrated to dryness to give 900 mg of 4-(2-aminooxyethyl)-N-tritylimidazole with mp 93° C. as a colorless powder.

Analysis for $C_{24}H_{23}N_3O.\frac{1}{2}H_2O$: Calculated: C 76.16, H 6.66, N 11.10; Found C 76.02, H 6.70, N 10.77

NMR (CDCl$_3$, δ, ppm): 2.84 (2H, t, J=9 Hz, —CH$_2$—C—), 3.90 (2H, t, J=9 Hz, —CH$_2$—O—), 5.37 (2H, br s, —NH$_2$), 6.61 (1H, s, C$_5$—H of imidazole), 7.10–7.40 (16H, m, trityl and C$_2$—H of imidazole)

900 mg of the above compound was added to a mixture of 950 mg of (2-tritylaminothiazol-4-yl)glyoxylic acid and 20 ml of methanol and then the resulting mixture was stirred for 5 hours at room temperature. Diisopropyl ether was added to the reaction mixture and the precipitate formed was collected by filtration to give 1.3 g of 2-(2-tritylaminothiazol-4-yl)-2-(2-(N-tritylimidazol-4-yl)ethoxyimino)acetic acid with decomposing point 200°–202° C. as colorless granular crystals.

Analysis for $C_{48}H_{39}N_5SO_3$: Calculated: C 75.27, H 5.13, N 9.14; Found: C 74.92, H 5.33, N 9.20

NMR (CDCl$_3$, δ, ppm): 2.93 (2H, t, J=8 Hz, —CH$_2$—C—), 4.48 (2H, t, J=8 Hz, —CH$_2$—O—), 6.69 (1H, s, C$_5$—H of imidazole), 6.84 (1H, s, C$_5$—H of thiazole), 7.86 (1H, s, C$_2$—H of imidazole).

Referential Example 3

1.96 g N-hydroxyphthalimide and 765 mg of 3-chloromethylpyrazole hydrochloride were added to a mixture of 0.28 g of sodium and 20 ml of ethanol under cooling in ice-bath and the resulting mixture was stirred for 2.5 hours at room temperature. The solvent was distilled off and water was added to the residue. The mixture was extracted with chloroform and the extract was washed with SSB and SSC and then dried with sodium sulfate. The solvent was distilled off and the residue was washed with ether to give 3-(phthalimidooxymethyl)pyrazole with mp 166°–168° C.

Analysis for $C_{12}H_9N_3O_3$: Calculated: C 59.26, H 3.73, N 17.28; Found: C 58.91, H 3.84, N 17.21

0.53 g of the above product was suspended in 20 ml of methylene chloride and 0.61 g of trityl chloride and 0.35 ml of triethylamine were added thereto at room temperature and then the resulting mixture was stirred for 3 hours. The reaction mixture was washed with 10% aqueous solution of citric acid and SSC and dried with sodium sulfate. The solvent was distilled off and the residue was washed with ether to give 0.89 g of 3-

(phthalimidooxymethyl)-N-tritylpyrazole with mp 177°–179° C.

IR: 1790, 1735

CW-NMR (CDCl$_3$, δ, ppm): 5.25 (2H, s, NOCH$_2$—), 6.52 (1H, d, J=2 Hz, C$_4$—H of pyrazole), 7.0–7.3 (16H, m, trityl and C$_5$—H of pyrazole), 7.72 (4H, s, phthalimide)

0.86 g of the above product was suspended in 20 ml of ethanol and 90 mg of hydrazine hydrate was added thereto and then the resulting mixture was stirred for one hour at 70° C. The insoluble material precipitated was removed by filtration and the solvent was distilled off. Ethyl acetate was added to the residue and the insoluble material was removed by filtration. The filtrate was washed with SSC and dried with sodium sulfate. The solvent was distilled off and the residue was washed with ether to give 0.64 g of 3-(aminooxymethyl)-N-tritylpyrazole with mp 105°–110° C.

IR: 3400, 1720, 1485, 1440

CW-NMR (CDCl$_3$, δ, ppm): 4.72 (2H, s, NO—CH$_2$—), 6.27 (1H, d, J=2 Hz, C$_4$—H of pyrazole), 7.1–7.4 (16H, m, trityl and C$_5$—pyrazole)

0.62 g of the above product was suspended in 20 ml of ethanol and 0.75 g of (2-tritylaminothiazol-4-yl)glyoxylic acid was added thereto and the resulting mixture was stirred for 3 hours at room temperature. The solvent was distilled off and ethyl acetate was added to the residue and the mixture was washed with a mixture of diluted hydrochloric acid and an aqueous solution of sodium chloride and then washed with SSC and dried with sodium sulfate. The solvent was distilled off and then residue was washed with ether to give 1.28 g of 2-(2-tritylaminothiazol-4-yl)-2-((N-tritylpyrazol-3-yl)methoxyimino)acetic acid with mp 143°–146° C.

IR: 1720, 1520

CW-NMR (CDCl$_3$, δ, ppm): 5.42 (2H, s, =N—O—CH$_2$—), 6.05 (1H, d, J=2 Hz, C$_4$—H of pyrazole), 6.53 (1H, s, C$_5$—H of thiazole), 7.0–7.4 (m, trityl and C$_5$—H of pyrazole)

Referential Example 4

0.78 g of ethyl pyrazole-4-carboxylate was dissolved in 15 ml of methylene chloride and 1.56 g of trityl chloride and 0.86 ml of triethylamine were added thereto and then the resulting mixture was stirred for 1.5 hours at room temperature. The reaction mixture was washed with 10% aqueous solution of citric acid and SSC and then dried with sodium sulfate. The solvent was distilled off to give 2.45 g of ethyl 1-tritylpyrazole-4-carboxylate as an oil.

CW-NMR (CDCl$_3$, δ, ppm): 1.30 (3H, t, J=7 Hz, —OCH$_2$CH$_3$), 4.26 (2H, q, J=7 Hz, —CH$_2$CH$_3$), 7.1–7.4 (15H, m, trityl), 7.92 (1H, s, C$_3$—H of pyrazole), 8.03 (1H, s, C$_5$—H of pyrazole)

A solution prepared by dissolving 2.45 g of the above product in THF was added to a mixture of 0.42 g of lithium aluminium hydride and 30 ml of THF under cooling in an ice-bath and then the resulting mixture was refluxed for one hour at 80° C. After cooling, water was added to the reaction mixture and the solvent was distilled off. The residue was dissolved in ethyl acetate and the mixture was washed with an aqueous solution of sodium chloride and dried with sodium sulfate. The solvent was distilled off and the residue was washed with ether to give 1.53 g of 4-hydroxymethyl-1-tritylpyrazole with mp 181°–184° C.

CW-NMR (CDCl$_3$, δ, ppm): 4.51 (2H, s, —O—CH$_2$—), 7.1–7.4 (16H, m, trityl and C$_3$—H of pyrazole), 7.63 (1H, s, C$_5$—H of pyrazole)

1.51 g of the above product was dissolved in 30 ml of THF, and 0.78 g of N-hydroxyphthalimide, 1.26 g of triphenylphosphine and 0.84 g of diethyl azodicarboxylate acid were added thereto at room temperature and then the resulting mixture was stirred for 30 minutes. The solvent was distilled off and the residue was purified by silica gel column chromatography with a mixture of ethyl acetate and benzene (1:4 volume) eluent to give 1.84 g of 4-(phthalimidooxymethyl)-1-tritylpyrazole with mp 186°–188° C.

Analysis for C$_{31}$H$_{23}$N$_3$O$_3$: Calculated: C 76.68, H 4.78, N 8.66; Found: C 76.90, H 4.94, N 8.64

IR: 1780, 1720

CW-NMR (CDCl$_3$, δ, ppm): 5.12 (2H, s, NOCH$_2$), 7.0–7.3 (15H, m, trityl), 7.51 (1H, s, C$_3$—H of pyrazole), 7.70 (1H, s, C$_5$—H of pyrazole), 7.73 (4H, s, phthalimide)

0.86 g of the above product was suspended in 20 ml of ethanol and 90 mg of hydrazine hydrate was added thereto. The resulting mixture was stirred for one hour at 70° C. The precipitate formed was removed by filtration and the filtrate was concentrated. Chloroform was added to the residue and the insoluble material was removed by filtration.

The filtrate was washed with SSC and dried with sodium sulfate. The solvent was distilled off to give 0.71 g of 4-aminooxymethyl-1-tritylpyrazole with mp 133°–136° C.

IR: 3400, 1720

CW-NMR (CDCl$_3$, δ, ppm): 4.53 (2H, s, NOCH$_2$), 7.0–7.4 (16H, m, trityl and C$_3$—H of pyrazole), 7.67 (1H, s, C$_5$—H of pyrazole)

0.71 g of the above product was suspended in 20 ml of ethanol and 0.75 g of (2-tritylaminothiazol-4-yl)glyoxylic acid was added portionwise thereto over a period of 4 hours. The solvent was distilled off and the residue was dissolved in chloroform. The mixture was dried with sodium sulfate and the solvent was distilled off. The residue was washed with ether to give 0.82 g of 2-(2-tritylaminothiazol-4-yl)-2-((1-tritylpyrazol-4-yl)methoxyimino)acetic acid with mp 130°–135° C.

IR: 1720, 1595

CW-NMR (CDCl$_3$, δ, ppm): 4.98 (2H, s, NOCH$_2$—), 6.40 (1H, s, C$_5$—H of thiazole), 7.1–7.3 (m, trityl), 7.36 (s, C$_3$—H of pyrazole), 7.61 (1H, s, C$_5$—H of pyrazole)

Referential Example 5

A mixture of 1 g of sodium and 80 ml of ethanol was cooled in an ice-bath and 7.12 g of N-hydroxyphthalimide was added thereto and the mixture was stirred at room temperature. The mixture was cooled in an ice-bath and 3.16 g of 5-methyl-4-chloromethylimidazole hydrochloride was added thereto. The resulting mixture was stirred for 2 hours. The solvent was distilled off and SSB was added to the residue and the mixture was extracted with chloroform. The extract was washed with SSC and dried with sodium sulfate and concentrated to dryness. The residue was washed with ether to give 2.37 g of N-((5-methylimidazole-4-yl)methoxy)phthalimide with mp 155°–156° C.

IR: 1780, 1730

CW-NMR (DMSO-d$_6$, δ, ppm): 2.20 (3H, s, methyl), 5.03 (2H, s, —CH$_2$O—), 7.46 (1H, s, C$_2$—H of imidazole), 7.83 (4H, s, phenyl)

2.10 g of the above product was dissolved in 150 ml of chloroform and then 2.27 g of trityl chloride and 1.70 ml of triethylamine was added thereto under cooling in an ice-bath. The mixture was stirred for 2 hours at room temperature. The reaction mixture was washed with SSB and SSC and dried with sodium sulfate and then concentrated to dryness. The residue was purified by silica gel column chromatography with chloroform eluent to give 1.26 g of N-((N-trityl-5-methylimidazol-4-yl)methoxy)phthalimide with mp 220°–223° C.

IR: 1730, 1440, 1360

CW-NMR (CDCl$_3$, δ, ppm): 2.40 (3H, s, methyl), 4.50 (2H, s, —CH$_2$O—), 7.30 (16H, s, C$_2$—H of imidazole and trityl), 7.70 (4H, s, phenyl)

1.26 g of the above product was dissolved in 30 ml of ethanol and 125 mg of hydrazine hydrate was added thereto and the resulting mixture was stirred at 80° C. for 2 hours. After cooling the precipitate formed was removed by filtration and the filtrate was concentrated to dryness. Water was added to the residue and the mixture was extracted with ethyl acetate. The extract was dried with sodium sulfate and concentrated to dryness. The residue was washed with ether to give 900 mg of 5-methyl-4-aminooxymethyl)-N-tritylimidazole with mp 75°–77° C.

IR: 1720, 1650, 1690, 1485, 1440

CW-NMR (CDCl$_3$, δ, ppm): 2.26 (3H, s, methyl), 4.05 (2H, s, —CH$_2$O—), 7.10–7.45 (16H, m, C$_2$—H of imidazole and trityl)

1.13 g of the above product was added to a mixture of 1.02 g of (2-tritylaminothiazol-4-yl)glyoxylic acid and 50 ml of ethanol and then the resulting mixture was stirred for 2 hours at room temperature. The white precipitate formed was collected by filtration and washed with ether to give 1.63 g of 2-(2-tritylaminothiazol-4-yl)-2-((5-methyl-N-tritylimidazol-4-yl)methoxyimino)acetic acid with mp 175°–176° C.

IR: 1740, 1600, 1540, 1490, 1450

CW-NMR (CDCl$_3$, δ, ppm): 2.35 (3H, s, C$_5$-methyl of imidazole), 4.50 (2H, s, —CH$_2$—O—), 6.00 (2H, br s, NH and —COOH), 6.66 (1H, s, C$_5$—H of thiazole), 7.10–7.45 (16H, m, C$_2$—H of imidazole and trityl)

Referential Example 6 9 g of 1-methyl-5hydroxymethylimidazole was dissolved in 300 ml of anhydrous THF and 13 g of N-hydroxyphthalimide and 21 g of triphenylphosphine were added thereto under stirring at room temperature. 15.3 g of diethyl azodicarboxylate was added dropwise to the mixture and the resulting mixture was stirred for 3 hours at room temperature. The solvent was distilled off and the residue was purified by silica gel column chromatography with 2% methanol-chloroform eluent to give 13.7 g of N-(1-methylimidazol-5-yl)methoxyphthalimide with mp 170°–171° C.

IR: 1780, 1725

CW-NMR (CDCl$_3$, δ, ppm): 3.90 (3H, s, CH$_3$), 5.17 (2H, s, CH$_2$O), 7.03 (1H, s, C$_4$—H of imidazole), 7.51 (1H, s, C$_2$—H of imidazole), 7.73 (4H, s, phenyl)

12.85 g of the above product was suspended in 300 ml of ethanol and 2.5 g of hydrazine hydrate was added thereto and then the resulting mixture was stirred overnight at room temperature. The insoluble material was removed by filtration and the filtrate was concentrated to dryness. The residue was added to a small amount of ethanol and the insoluble material was removed by filtration and then the filtrate was concentrated to dryness. Chloroform was added to the residue and the insoluble material was removed by filtration and the filtrate was purified by silica gel column chromatography with 1% methanol-chloroform eluent to give 5.51 g of 5-aminooxymethyl-1-methylimidazole.

CW-NMR (CDCl$_3$, δ, ppm): 3.65 (3H, s, CH$_3$), 4.63 (2H, s, CH$_2$O), 5.34 (2H, br s, NH$_2$), 7.04 (1H, s, C$_4$—H of imidazole) 7.41 (1H, s, C$_2$—H of imidazole)

17.4 g of (2-tritylaminothiazol-4-yl)glyoxylic acid was dissolved in 500 ml of methanol under heating and the mixture was cooled to room temperature. A mixture of 100 ml of methanol and 5.5 g of 5-aminooxymethyl-1-methylimidazole was added to the mixture and then the resulting mixture was stirred overnight at room temperature. The precipitate formed was collected by filtration and washed with methanol to give 14.9 g of 2-(2-tritylaminothiazol-4-yl)-2-((1-methylimidazol-5-yl)methoxyimino)acetic acid with mp 231°–232° C. (decomposition).

IR: 1615, 1530

Referential Example 7

Using procedures analogous to that described in Referential Example 1, 2-(2-tritylaminothiazol-4-yl)-2-((2-methyl-N-tritylimidazol-4-yl)methoxyimino)acetic acid with mp 192°–193° C. was obtained.

IR: 1740, 1600, 1540

CW-NMR (CDCl$_3$, δ, ppm): 1.73 (3H, s, C$_2$—CH$_3$ of imidazole), 5.26 (2H, s, CH$_2$O—), 6.62 (1H, s, C$_5$—H of thiazole), 6.90 (1H, s, C$_5$—H of imidazole), 7.00–7.40 (30H, m, trityl)

Referential Example 8

4.6 g of lithium aluminium hydride was suspended in 200 ml of anhydrous THF, and a mixture of 100 ml of THF and 16 g of ethyl 1-methylpyrazole-3-carboxylate was added dropwise wise thereto at 0° C. The resulting mixture was stirred for one hour at room temperature. Hydrous ether was added to the reaction mixture for decomposing the excess lithium aluminium hydride. The insoluble material was removed by filtration and the filtrate was concentrated. 500 ml of chloroform was added to the mixture and the resulting mixture was dried with sodium sulfate and concentrated to dryness to give 12 g of 1-methyl-3-hydroxy methylpyrazole as an oil.

CW-NMR (CDCl$_3$, δ, ppm): 3.81 (3H, s, NCH$_3$), 4.61 (2H, s, CH$_2$O), 6.20 (1H, d, J=2 Hz, C$_4$—H of pyrazole), 7.25 (1H, d, J=2 Hz, C$_5$—H of pyrazole)

9 ml of thionyl chloride was added dropwise to 12 g of the above product under cooling in an ice-bath and the resulting mixture was heated at 90° C. for 15 minutes to give a solid residue. Ether was added to the residue and the residue was triturated. The precipitate formed was collected by filtration and washed with ether and then dried to give 14 g of 1-methyl-3-chloromethyl-pyrazole hydrochloride with mp 94°–97° C.

CW-NMR (D$_2$O, δ, ppm): 3.98 (3H, s, NCH$_3$), 4.70 (2H, s, CH$_2$O), 6.57 (1H, d, J=2 Hz, C$_4$—H of pyrazole), 7.82 (1H, d, J=2 Hz, C$_5$—H of pyrazole)

4.5 g of potassium carbonate and 200 mg of 18-Crown-6 were added to a mixture of 3.5 g of N-hydroxyphthalimide and 30 ml of DMF. A mixture of 3 g of the above product and 30 ml of DMF was added thereto and then the resulting mixture was stirred for 15 hours at 60° C. The insoluble material was removed by filtration and the filtrate was concentrated to dryness. Chloroform and SSB were added to the residue. The organic solvent layer was washed with water and dried with sodium sulfate and concentrated to dryness. The residue was treated with ether to give 3.5 g of 1-methyl-3-phthalimidooxymethylpyrazole as a powder with mp 122°–124° C.

CW-NMR (CDCl$_3$, δ, ppm): 3.82 (3H, s, NCH$_3$), 5.21 (2H, s, CH$_2$O), 6.45 (1H, d, J=2 Hz, C$_4$—H of pyrazole), 7.32 (1H, d, J=2 Hz, C$_5$—H of pyrazole), 7.76 (4H, s, phenyl)

3.3 g of the above product was dissolved in 60 ml of 6 normal hydrochloric acid and the mixture was refluxed for one hour. The reaction mixture was cooled in an ice-bath. The precipitate formed was removed by filtration and the filtrate was concentrated to dryness. The residue was treated with ether to give 2.5 g of 1-methyl-3-aminooxymethylpyrazole dihydrochloride as a powder with mp 112°–115° C.

CW-NMR (D$_2$O, δ, ppm) 4.02 (3H, s, NCH$_3$) 5.20 (2H, s, CH$_2$O) 6.64 (1H, d, J=2 Hz, C$_4$—H of pyrazole) 7.80 (1H, d, J=2 Hz, C$_5$—H of pyrazole)

2.4 g of the above product was dissolved in 7 ml of water and 2 g of sodium bicarbonate was added thereto in small portions. The mixture was added to a mixture of 4.5 g of (2-tritylaminothiazol-4-yl)glyoxylic acid and 150 ml of methanol. The resulting mixture was stirred for 5 hours at room temperature. The solvent was distilled off and the residue was dissolved in chloroform. The mixture was washed with water and dried with sodium sulfate and then the solvent was distilled off. The residue was treated with ether to give 5 g of 2-(2-tritylaminothiazol-4-yl)-2-((1-methylpyrazol-3-yl)methoxyimino)acetic acid as a powder with mp 125°–132° C. (decomposition).

CW-NMR (CDCl$_3$, δ, ppm): 3.79 (3H, s, NCH$_3$), 5.27 (2H, s, CH$_2$O), 6.11 (1H, d, J=1.5 Hz, C$_4$—H of pyrazole), 6.65 (1H, s, C$_5$—H of thiazole), 7.27 (16H, s, trityl and C$_5$—H of pyrazole)

Referential Example 9

Using procedures analogous to that described in Referential Example 8, 2-(2-tritylaminothiazol-4-yl)-2-((1-methylpyrazol-5-yl)methoxyimino)acetic acid with mp 176°–180° C. (decomposition) was obtained.

CW-NMR (CDCl$_3$, δ, ppm): 3.69 (3H, s, N—CH$_3$), 5.11 (2H, s, CH$_2$O), 6.16 (1H, s, C$_4$—H of pyrazole), 6.52 (1H, s, C$_5$—H of thiazole)

Referential Example 10

3.47 g of ethyl 1,2,3-triazole-4-carboxylate and 7.55 g of trityl chloride were dissolved in 100 ml of chloroform and 3.77 ml of triethylamine was added dropwise thereto under stirring and cooling in an ice-bath. The resulting mixture was stirred for 30 minutes at room temperature. Chloroform was distilled off and the residue was dissolved in ethyl acetate and the mixture was washed with an aqueous solution of sodium chloride and then dried with sodium sulfate. Ethyl acetate was distilled off and the residue was purified by silica gel column chromatography with benzene and chloroform eluent to give 8.37 g of ethyl N-trityl-1,2,3-triazole-4-carboxylate with mp 201°–203° C.

IR: 1730

CW-NMR (CDCl$_3$, δ, ppm): 1.37 (3H, t, J=7.5 Hz, CH$_2$CH$_3$), 4.39 (2H, q, J=7.5 Hz, CH$_2$CH$_3$), 8.01 (1H, s, C$_5$—H of triazole), A mixture of 13.0 g of the above product and 300 ml of THF was added dropwise to a mixture of 1.29 g of lithium aluminium hydride and 100 ml of THF under stirring and cooling in an ice-bath and the resulting mixture was stirred for 3 hours at room temperature. 1.3 ml of water, 1.3 ml of a 15% aqueous solution of sodium hydroxide and 3.0 ml of water were added carefully to the reaction mixture. The insoluble material was removed by filtration and the filtrate was concentrated to dryness in vacuo. n-Hexane was added to the residue. The precipitate formed was collected by filtration and washed with n-hexane and then dried in vacuo to give 11.4 g of 4-hydroxymethyl-N-trityl-1,2,3-triazole with mp 205°–207° C.

IR: 3600–3100, 1445

CW-NMR (CDCl$_3$, δ, ppm): 4.78 (2H, s, —OCH$_2$—)

17.5 g of the above product, 8.4 g of N-hydroxyphthalimide and 14.8 g of triphenylphosphine were dissolved in 700 ml of THF and 9.8 g of diethyl azodicarboxylate was added thereto. The resulting mixture was stirred for one hour at room temperature. The solvent was distilled off and chloroform was added to the residue. The mixture was concentrated to dryness in vacuo and ether was added to the residue. The precipitate formed was collected by filtration and dried in vacuo and then dissolved in methylene chloride. The precipitate formed was collected by filtration and dried in vacuo to give 24.5 g of the product as a powder. The product was purified by silica gel column chromatography with chloroform eluent to give 14.2 g of 4-phthalimidooxymethyl-N-trityl-1,2,3-triazole with mp 195°–200° C.

IR: 1790, 1730

CW-NMR (CDCl$_3$, δ, ppm): 5.36 (2H, s, OCH$_2$)

16.2 g of the above product was suspended in 300 ml of methanol and 1.7 g of hydrazine hydrate was added thereto and then the resulting mixture was stirred for 1.5 hours at room temperature. The insoluble material was removed by filtration and the solvent was distilled off. Chloroform was added to the residue and the insoluble material was removed by filtration and the filtrate was concentrated to dryness in vacuo. These procedures comprising dissolving and filtration were carried out 3–4 times. The final residue was purified by silica gel column chromatography with chloroform eluent to give 9.5 g of 4-aminooxymethyl-N-trityl-1,2,3-triazole with mp 144°–145° C.

IR: 3600–3200

CW-NMR (CDCl$_3$, δ, ppm): 4.79 (2H, s, OCH$_2$), 4.80–5.80 (2H, br s, NH$_2$), 7.45 (1H, s, C$_5$—H of triazole)

2.58 g of the above product was dissolved in 100 ml of methanol and 2.48 g of (2-tritylaminothiazol-4-yl)glyoxylic acid was added thereto under stirring at room temperature and the resulting mixture was stirred for 16 hours. The solvent was distilled off and the residue was dissolved in ethyl acetate. The mixture was washed with hydrochloric acid adjusted to pH 4 and an aqueous solution of sodium chloride and dried with sodium sulfate. The solvent was distilled off and the residue was dissolved in a small amount of chloroform and n-Hexane was added thereto. The precipitate formed was collected by filtration and washed with n-Hexane and dried in vacuo to give 4.05 g of 2-(2-tritylaminothiazol-4-yl)-2-((N-trityl-1,2,3-triazol-4-yl)methoxyimino)acetic acid with mp 133°–145° C. (decomposition)

IR: 3600–2700, 1720

CW-NMR (CDCl$_3$, δ, ppm): 5.27 (2H, s, OCH$_2$), 6.55 (1H, s, C$_5$—H of thiazole)

Example 1

A mixture of methylene chloride and 209 mg of phosphorus pentachloride was cooled to −10° C. and 752 mg of 2-(2-tritylaminothiazol-4-yl)2-(N-tritylimidazol-4-yl)methoxyimino)acetic acid was added thereto and the mixture was stirred for 10 minutes at the same temperature. 0.25 ml of triethylamine was added to the mixture and after 5 minutes a mixture of methylene chloride, 401 mg of tertiary butyl 7-amino-3-bromomethyl-3-cephem-4-carboxylate 1-oxide hydrochloride and 0.14 ml of triethylamine was added thereto. The resulting mixture was stirred for 30 minutes at the same temperature. A 5% aqueous solution of sodium bicarbonate was added to the reaction mixture and the organic solvent layer was washed with a diluted aqueous solution of citric acid and SSC and dried with sodium sulfate and then concentrated to dryness to give 1.0 g of tertiary butyl 7β-(2-(2-tritylaminothiazol-4-yl)-2-((N-tritylimidazol-4-yl)methoxyimino)acetamido)-3-bromomethyl-3-cephem-4-carboxylate 1-oxide (syn isomer).

IR: 1795, 1715, 1675

CW-NMR (CDCl$_3$, δ, ppm): 1.55 (9H, s, —COOC(CH$_3$)$_3$), 4.65 (1H, d, J=5 Hz, C$_6$—H), 5.32 (2H, s, —O—CH$_2$—), 6.70 (1H, s, C$_5$—H of thiazole), 6.74–7.60 (m, trityl and imidazole)

1.0 g of the above product was dissolved in acetone and 1.2 ml of pyridine was added thereto. The resulting mixture was stirred overnight at room temperature. Ether was added to the reaction mixture and the precipitate formed was collected by filtration and dried. 880 mg of the product was dissolved in DMF and the mixture was cooled to −50° C. 0.2 ml of phosphorus trichloride was added thereto under stirring and the temperature of the mixture was raised to −20° C. Nextly the mixture was cooled to −70° C. and ethyl acetate was added thereto. The resulting mixture was washed with water at room temperature and dried with sodium sulfate and concentrated to dryness. Formic acid and a small amount of hydrochloric acid was added to the residue and the mixture was stirred for one hour. The reaction mixture was concentrated and acetone was added thereto. The precipitate formed was collected by filtration and purified by HPLC using Partisil as a support with water eluent to give 7β-(2-(2-aminothiazol-4-yl)-2-((imidazol-4-yl)methoxyimino)acetamido)-3-(1-pyridinio)methyl-3-cephem-4-carboxylate trihydrochloride (syn isomer).

FT-NMR (D$_2$O, δ, ppm, 200 MHz): 5.32 (1H, d, J=5 Hz, C$_6$—H), 5.42 (2H, s, —OCH$_2$—), 5.90 (1H, d, J=5 Hz, C$_7$—H), 7.23 (1H, s, C$_5$—H of thiazole), 7.64 (1H, s, C$_5$—H of imidazole), 8.16 (2H, t, J=6 Hz, C$_3$ and C$_5$—H of pyridine), 8.65 (1H, t, J=6 Hz, C$_4$—H of pyridine), 8.78 (1H, s, C$_2$—H of imidazole), 9.00 (2H, d, J=6 Hz, C$_2$ and C$_6$—H of pyridine)

Example 2

204 mg of 1-hydroxybenzotriazole and 274 mg of DCC were added to a mixture of DMF and 1.0 g of 2-(2-tritylaminothiazol-4-yl)-2-((N-tritylimidazol-4-yl)methoxyimino)acetic acid and then the resulting mixture was stirred for 5 hours at room temperature. The insoluble material was removed by filtration and a mixture of DMF, 442 mg of triethylamine and 442 mg of 7β-amino-3-(1-methyl-1H-tetrazol-5-yl)thiomethyl-3-cephem-4-carboxylic acid was added to the filtrate and the resulting mixture was stirred overnight. The solvent was distilled off and ethyl acetate was added to the residue and the mixture was washed with water and dried with sodium sulfate and then concentrated to dryness. Ether was added to the residue and the insoluble material was collected by filtration to give 630 mg of a powder.

The powder was dissolved in 50 ml of formic acid and 2 ml of concentrated hydrochloric acid was added thereto and the resulting mixture was stirred for 2 hours at room temperature. The reaction mixture was concentrated to dryness and the residue was purified by HPLC using Bondapak as a support with 15% aqueous solution of methanol eluent (adjusted to pH3 with hydrochloric acid) to give 7β-(2-(2-aminothiazol-4-yl)-2-((imidazol-4-yl)methoxyimino)acetamido)-3-(1-methyl-1H-tetrazol-5-yl)thiomethyl-3-cephem-4-carboxylic acid dihydrochloride (syn isomer).

IR: 1775 (CO)

FT-NMR (D$_2$O, δ, ppm, 200 MHz): 3.75 (2H, AB-q, J=16 Hz, C$_2$—H), 4.10 (3H, s, —CH$_3$), 5.23 (1H, d, J=5 Hz, C$_6$—H), 5.43 (2H, s, —O—CH$_2$—), 5.80 (1H, d, J=5 Hz, C$_7$—H), 7.24 (1H, s, C$_5$—H of thiazole), 7.66 (1H, s, C$_5$—H of imidazole), 8.80 (1H, s, C$_2$—H of imidazole)

Example 3

Using procedures analogous to that described in Example 1, 7β-(2-(2-aminothiazol-4-yl)-2-(2-imidazol-4-yl)ethoxyimino)acetamido)-3-(1-pyridinio)methyl-3-cephem-4-carboxylate trihydrochloride (syn isomer) with decomposing point 180°–195° C. as a colorless powder was obtained.

Analysis for C$_{23}$H$_{22}$N$_8$S$_2$O$_5$.3HCl.5H$_2$O: Calculated: C 36.63, H 4.27, N 14.86; Found: C 36.81, H 3.97, N 15.10

FT-NMR (D$_2$O, δ, ppm): 3.19 (2H, t, J=6 Hz, —CH$_2$—CH$_2$—O), 3.26 (1H, d, J=17 Hz, C$_2$—H), 3.68 (1H, d, J=17 Hz, C$_2$—H), 3.58 (2H, t, J=6 Hz, —CH$_2$—O—), 5.28 (1H, d, J=5 Hz, C$_6$—H), 5.44 (1H, d, J=14 Hz,

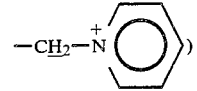

5.64 (1H, d, J=14 Hz,

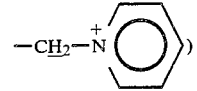

5.85 (1H, d, J=5 Hz, C$_7$—H), 7.15 (1H, s, C$_5$—H of thiazole), 7.30 (1H, s, C$_5$—H of imidazole), 8.64 (1H, s, C$_2$—H of imidazole), 8.14 (2H, t, J=7 Hz, C$_3$ and C$_5$—H of pyridine), 8.64 (1H, t, J=7 Hz, C$_4$—H of pyridine), 8.99 (2H, d, J=7 Hz, C$_2$ and C$_6$—H of pyridine)

Example 4

0.77 ml of DMF and 0.91 ml of phosphorus oxychloride were added to ethyl acetate under cooling in an ice-bath to make the volume to 10 ml. 1.20 g of 2-(2-tritylaminothiazol-4-yl)-2-((N-tritylpyrazol-3-yl)methoxyimino)acetic acid was dissolved in 5 ml of ethyl acetate and 3.0 ml of the above mixture was added thereto under cooling in an ice-bath and the resulting mixture was stirred for 50 minutes. The reaction mixture was added to a mixture of 1.1 g of 7β-amino-3-(1-pyridinio)methyl-3-cephem-4-carboxylate dihydrochloride, 1.2 ml of N,O-bis(trimethylsilyl)acetamide and 8 ml of acetonitrile under cooling in an ice-bath. After 15 minutes the temperature of the mixture was raised to room temperature and the mixture was stirred for two hours. An aqueous solution of sodium chloride was added to the reaction mixture and ethyl acetate was distilled off in vacuo and the mixture was extracted with chloroform. The extract was dried with sodium sulfate and the solvent was distilled off. The residue was washed with ether to give 1.65 g of a light brown powder. 20 ml of 98% formic acid and 1 ml of concentrated hydrochloric acid were added to the powder and the resulting mixture was stirred for 45 minutes at room temperature. The precipitate formed was removed by filtration and the filtrate was concentrated to dryness in vacuo. The residue was purified by column chromatography using HP-20 as a support with a 5% aqueous solution of THF eluent and nextly purified by HPLC using Partisil as a supporat with a 10% aqueous solution of methanol eluent to give 120 mg of 7β-(2-(2-aminothiazol-4-yl)-2-((pyrazol-3-yl)methoxyimino)acetamido)-3-(1-pyridinio)methyl-3-cephem-4-carboxylate (syn isomer) with mp 150°-170° C. (decomposition).

Analysis for $C_{22}H_{20}N_8O_5S_2 \cdot H_2O$: Calculated: C 47.30, H 3.97, N 20.06; Found: C 47.25, H 4.32, N 19.64
IR: 3400-2800, 1770, 1660, 1610, 1525
FT-NMR ($D_2O$, δ, ppm, 200 MHz): 3.12 (1H, d, J=18 Hz, $C_2$—H), 3.60 (1H, d, J=18 Hz, $C_2$—H), 5.23 (1H, d, J=5 Hz, $C_6$—H), 5.26 (2H, s, N—O—$CH_2$—), 5.36 (1H, d, J=14 Hz,

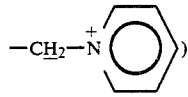

5.57 (1H, d, J=14 Hz,

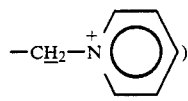

5.83 (1H, d, J=5 Hz, $C_7$—H), 6.47 (1H, d, J=2 Hz, $C_4$—H of pyrazole), 6.98 (1H, s, $C_5$—H of thiazole), 7.63 (1H, d, J=2 Hz, $C_5$—H of pyrazole), 8.10 (2H, t, J=7 Hz, $C_3$ and $C_5$—H of pyridine), 8.59 (1H, t, J=7 Hz, $C_4$—H of pyridine), 8.96 (2H, d, J=7 Hz, $C_2$ and $C_6$—H of pyridine)

Example 5

420 mg of phosphorus pentachloride was dissolved in 70 ml of chloroform and the mixture was cooled to −25° to −30° C. 1.51 g of 2-(2-tritylaminothiazol-4-yl)-2-((N-tritylpyrazol-3-yl)methoxyimino)acetic acid was added to the mixture and the resulting mixture was stirred for 30 minutes at the same temperature. 0.5 ml of triethylamine was added to the mixture and, after 3 minutes, a mixture of 810 mg of tertiary butyl 7β-amino-3-bromomethyl-3-cephem-4-carboxylate 1-oxide hydrochloride, 0.28 ml of triethylamine and methylene chloride was added to the mixture. The resulting mixture was stirred for 40 minutes at the same temperature. 50 ml of chloroform cooled in an ice-bath was added to the reaction mixture and the mixture was washed with water, a 3% aqueous solution of sodium bicarbonate and SSC and dried with sodium sulfate and then concentrated to dryness. The residue was purified by silica gel column chromatography using chloroform and nextly a mixture of chloroform and ethyl acetate (4:1 by volume) as an eluent solvent to give 1.92 g of tertiary butyl 7β-(2-(2-tritylaminothiazol-4-yl)-2-((N-tritylpyrazol-3-yl)methoxyimino)acetamido)-3-bromomethyl-3-cephem-4-carboxylate 1-oxide (syn isomer).
IR: 1800
FT-NMR (CDCl$_3$, δ, ppm, 200 MHz): 1.58 (9H, s, tertiary butyl), 2.97, 3.31 (each 1H, d, J=18 Hz $C_2$—H), 4.89 (1H, d, J=6 Hz, $C_6$—H), 5.44 (2H, s, —O—$CH_2$—), 6.10 (1H, dd, J=3 Hz, 6 Hz, $C_7$—H)

1.90 g of the above product was dissolved in 50 ml of acetone and 1.7 ml of pyridine was added thereto under cooling in an ice-bath and the resulting mixture was stirred for 14 hours at room temperature. The solvent was distilled off and the residue was dissolved in 3 ml of acetone. About 40 ml of ether was added to the mixture under stirring and the precipitate formed was collected by filtration to give 1.53 g of tertiary butyl 7β-(2-(2-tritylaminothiazol-4-yl)-2-(N-tritylpyrazol-3-yl)methoxyimino)acetamido)-3-(1-pyridinio)methyl-3-cephem-4-carboxoylate 1-oxide bromide (syn isomer).
IR: 1790
FT-NMR (CDCl$_3$, δ, ppm, 200 MHz): 1.57 (9H, s, tertiary butyl), 3.70, 4.13 (each 1H, d, J=18 Hz, $C_2$—H), 5.40 (2H, s, —O—$CH_2$—), 6.25 (1H, dd, J=3 Hz, 6 Hz, $C_7$—H)

1.10 g of the above product was dissolved in 15 ml of DMF and the mixture was cooled to −50° to −60° C. 0.24 ml of phosphorus trichloride was added to the mixture under stirring and the resulting mixture was stirred for 30 minutes at −40° to −50° C. The mixture was cooled to −50° to −60° C. and 50 ml of chloroform was added to the mixture. The resulting mixture was washed two times with SSC and with water. The organic solvent layer was dried with sodium sulfate and the solvent was distilled off. The residue was suspended in 1.9 ml of anisole and 6 ml of trifluoroacetic acid was added thereto under stirring at −30° to −40° C. The mixture was stirred for 30 minutes in an ice-bath and further stirred for 3 hours at room temperature. The reaction mixture was added to 30 ml of isopropyl ether cooled in an ice-bath and the precipitate formed was collected by filtration. 589 mg of the powder thus obtained was dissolved in 13 ml of water and the solution was adjusted to pH 7-8 with a 3% aqueous solution of sodium bicarbonate. The solution was set on a column packed with 70 ml of HP-20 and adsorbed. 342 mg of a powder obtained from a 5% aqueous solution of THF eluate was purified by HPLC using Bondapak as a support with a 15% aqueous solution of methanol eluent to give 190 mg of 7β-(2-(2-aminothiazol-4-yl)-2-((pyrazol-3-yl)methoxyimino)acetamido)-3-(1-pyridinio)methyl-3-cephem-4-carboxylate (syn isomer). The NMR and TLC data of the product was identical with those of the product obtained at Example 4.

Example 6

230 mg of phosphorus pentachloride was suspended in 20 ml of methylene chloride and the mixture was cooled to −30° C. A mixture of methylene chloride and 0.80 g of 2-(2-tritylaminothiazol-4-yl)-2-((1-tritylpyrazol-4-yl)methoxyimino)acetic acid was added thereto and the resulting mixture was stirred for 20 minutes at the same temperature. The reaction mixture was added to a mixture of 0.75 g of 7β-amino-3-(1-pyridinio)methyl-3-cephem-4-carboxylate dihydrochloride, 1.2 ml of N,O bis(trimethylsilyl)acetamide and 8 ml of acetonitrile, cooled in an ice-bath, and the resulting mixture was stirred for 3 hours. The reaction mixture was diluted with chloroform. The mixture was washed with SSC and dried with sodium sulfate and the solvent was distilled off. The residue was washed with ether to give 1.12 g of a light brown powder. The powder was added to a mixture of 12 ml of 98% formic acid and 0.6 ml of concentrated hydrochloric acid, cooled in an ice-bath, and the mixture was stirred for one hour at room temperature. The precipitate formed was removed by filtration and the filtrate was concentrated to dryness in vacuo. The residue was purified by column chromatography using 100 ml of HP-20 as a support with a 5% aqueous solution of THF eluent and nextly purified by HPLC using Partisil as a support with a 15% aqueous solution of methanol eluent to give 7β-(2-(2-aminothiazol-4-yl)-2-((pyrazol-4-yl)methoxyimino)acetamido)-3-(1-pyridinio)methyl-3-cephem-4-carboxylate (syn isomer) with mp 150°–165° C. (decomposition).

Analysis for $C_{22}H_{20}N_8O_2S_2.5/2H_2O$: Calculated: C 45.12, H 4.30, N 19.14; Found: C 45.29, H 4.22, N 19.25

IR: 3400–3100, 1770, 1660, 1605

FT-NMR ($D_2O$, δ, ppm, 200 MHz): 3.15 (1H, d, J=18 Hz, $C_2$—H), 3.60 (1H, d, J=18 Hz, $C_2$—H), 5.21 (2H, s, =$NOCH_2$—), 5.22 (1H, d, J=5 Hz, $C_6$—H), 5.39 (1H, d, J=14 Hz,

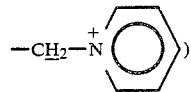

5.58 (1H, d, J=14 Hz,

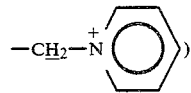

5.84 (1H, d, J=5 Hz, $C_7$—H), 7.01 (1H, s, $C_5$—H of thiazole), 7.78 (2H, s, $C_3$ and $C_5$—H of pyrazole), 8.14 (2H, t, J=7 Hz, $C_3$ and $C_5$—H of pyridine), 8.62 (1H, t, J=7 Hz, $C_4$—H of pyridine), 8.97 (2H, d, J=7 Hz, $C_2$ and $C_6$—H of pyridine)

Example 7

0.42 g of phosphorus pentachloride was added to a mixture of methylene chloride and 1.50 g of 2-(2-tritylaminothiazol-4-yl)-2-((N-tritylpyrazol-3-yl)methoxyimino)acetic acid under cooling to −40° C. and the mixture was stirred for 20 minutes at −20° to −30° C. 0.5 ml of triethylamine was added to the mixture and a mixture of methylene chloride, 0.80 g of tertiary butyl 7β-amino-3-bromomethyl-3-cepheme-4-carboxylate 1-oxide hydrochloride and 0.28 ml of triethylamine was added to the mixture and then the resulting mixture was stirred for 30 minutes at about −50° C. The reaction mixture was washed with a 5% aqueous solution of sodium bicarbonate, SSC, diluted hydrochloric acid and again SSC and dried with sodium sulfate. The solvent was distilled off and the oily product was dissolved in 60 ml of acetone. 2.44 g of 4-carbamoylpyridine was added to the mixture and the resulting mixture was stirred for 20 hours at room temperature. The solvent was distilled off and chloroform was added to the residue. The insoluble material was removed by filtration and the filtrate was washed with water, diluted hydrochloric acid and SSC and then dried with sodium sulfate. The solvent was distilled off and the residue was purified by silica gel column chromatography with a 15% methanol-chloroform eluent to give 0.42 g of tertiary butyl 7β-(2-(2-tritylaminothiazol-4-yl)-2-((N-tritylpyrazol-3-yl)methoxyimino)acetamido)-3-(4-carbamoyl-1-pyridinio)methyl-3-cephem-4-carboxylate 1-oxide bromide (syn isomer).

0.42 g of the above product was dissolved in 5 ml of DMF and 0.1 ml of phosphorus trichloride was added to the mixture under cooling at about −60° C. and then the resulting mixture was stirred for 30 minutes. The temperature of the mixture was raised to about −30° C. Chloroform was added to the reaction mixture and the mixture was washed with ice and dried with sodium sulfate. The solvent was distilled off and the residue was dried in vacuo to give 400 mg of an oil. The product was dissolved in 4 ml of 98% formic acid and 0.3 ml of concentrated hydrochloric acid was added to the mixture under cooling in an ice-bath, and then the resulting mixture was stirred for 15 hours at room temperature. Acetone was added to the reaction mixture under cooling in an ice-bath until the mixture turned into a transparent mixture. A large quantity of ether was added to the mixture and the precipitate formed was collected by filtration to give 230 mg of a light yellow powder. The powder was purified by column chromatography using HP-20 as a support with a 5% aqueous solution of THF eluent and HPLC using Particil as a support with a 12% aqueous solution of methanol eluent to give 124 mg of 7β-(2-(2-aminothiazol-4-yl)-2-((pyrazol-3-yl)methoxyimino)acetamido)-3-(4-carbamoyl-1-pyridinio)methyl-3-cephem-4-carboxylate (syn isomer) with mp 160°–175° C. (decomposition).

Analysis for $C_{23}H_{21}N_9O_6S_2.3H_2O$: Calculated C 43.32, H 4.27, N 19.77; Found C 43.19, H 3.88, N 19.70

IR: 3400, 1770, 1660, 1610

FT-NMR ($D_2O$+DCl, δ, ppm, 200 MHz): 3.22 (1H, d, J=18 Hz, $C_2$—H), 3.70 (1H, d, J=18 Hz, $C_2$—H), 5.28 (1H, d, J=5 Hz, $C_6$—H), 5.35 (2H, s, =$NOCH_2$—), 5.46 (1H, d, J=14 Hz,

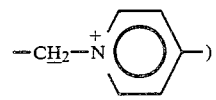

5.71 (1H, d, J=14 Hz,

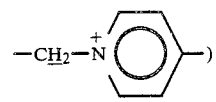

5.87 (1H, d, J=5 Hz, $C_7$—H) 6.54 (1H, d, J=2 Hz, $C_4$—H of pyrazole) 7.17 (1H, s, $C_5$—H of thiazole) 7.73 (1H, d, J=2 Hz, $C_5$—H of pyrazole) 8.44 (2H, d, J=7 Hz, $C_3$ and $C_5$—H of pyridine) 9.18 (2H, d, J=7 Hz, $C_2$ and $C_6$—H of pyridine)

Example 8

A mixture of methylene chloride and 209 mg of phosphorus pentachloride was cooled to $-10°$ C. 752 mg of 2-(2-tritylaminothiazol-4-yl)-2-((N-tritylimidazol-4-yl)methoxyimino)acetic acid was added to the mixture and the mixture was stirred for 10 minutes at the same temperature. 0.25 ml of triethylamine was added thereto and after 5 minutes a mixture of methylene chloride, 401 mg of tertiary butyl 7β-amino-3-bromomethyl-3-cephem-4-carboxylate 1-oxide hydrochloride and 0.14 ml of triethylamine was added to the mixture. The resulting mixture was stirred for 30 minutes at the same temperature. A 5% aqueous solution of sodium bicarbonate was added to the reaction mixture and the organic solvent layer was washed with a diluted aqueous solution of citric acid and SSC and dried with sodium sulfate and then concentrated to dryness to give 1.0 g tertiary butyl 7β-(2-(2-tritylaminothiazol-4-yl)-2-((N-tritylimidazol-4-yl)methoxyimino)acetamido)-3-bromomethyl-3-cephem-4-carboxylate 1-oxide (syn isomer).

IR: 1795, 1715, 1675

CW-NMR (CDCl$_3$, δ, ppm): 1.55 (9H, s, —COOC(CH$_3$)$_3$), 4.65 (1H, d, J=5 Hz, C$_6$—H), 5.32 (2H, s, —O—CH$_2$—), 6.70 (1H, s, C$_5$—H of thiazole), 6.74–7.60 (m, trityl and imidazole)

2.19 g of the above product was dissolved in acetone and 2.44 g of 4-carbamoylpyridine was added thereto and the resulting mixture was stirred overnight at room temperature. Acetone was distilled off and the chloroform was added to the residue. The insoluble material was removed by filtration, and the filtrate was washed with hydrochloric acid adjusted to pH 3 and SSC, dried with sodium sulfate and then concentrated to dryness. The residue was purified by silica gel column chromatography with a 15% methanol-chloroform eluent to give 0.98 g of product as an oil.

The above product was dissolved in 12 ml of DMF and the mixtue was cooled to $-60°$ C. 0.22 ml of phosphorus trichloride was added thereto and the temperature of the mixture was raised to $-30°$ C. The mixture was cooled to $-60°$ C. and ethyl acetate was added thereto and the resulting mixture was washed with water. The organic solvent layer was dried with sodium sulfate and concentrated to dryness to give 0.80 g of the product as an oil.

1.2 ml of anisole and 10 ml of trifluoroacetic acid were added to the above product under cooling in an ice-bath with stirring and the resulting mixture was stirred for 1.5 hours at room temperature. The reaction mixture was concentrated to dryness in vacuo and ether was added to the residue and then precipitate formed was collected by filtration. The precipitate was dried in vacuo and dissolved in 6 ml of formic acid and 0.4 ml of concentrated hydrochloric acid was added thereto under cooling in an ice-bath with stirring and then the resulting mixture was stirred for 30 minutes at room temperature. Acetone and ether were added to the reaction mixture and the precipitate formed was collected by filtration and the powder obtained was purified by column chromatography using HP-20 as a support and HPLC using Partisil as a support with water eluent (adjusted to pH 2–3 with hydrochloric acid) to give 7β-(2-(2-aminothiazol-4-yl)-2-((imidazol-4-yl)methoxyimino)acetamido)-3-(4-carbamoyl-1-pyridinio)methyl-3-cephem-4-carboxylate trihydrochloride (syn isomer).

IR: 1775, 1680

FT-NMR (D$_2$O, δ, ppm, 200 MHz): 5.31 (1H, d, J=4.5 Hz, C$_6$—H), 5.39 (2H, s, —O—CH$_2$—), 5.89 (1H, d, J=4.5 Hz, C$_7$—H), 7.20 (1H, s, C$_5$—H of thiazole), 7.62 (1H, s, C$_5$—H of imidazole), 8.42 (2H, d, J=6 Hz, C$_3$—H of pyridine), 8.75 (1H, s, C$_2$—H of imidazole), 9.17 (2H, d, J=6 Hz, C$_2$—H of pyridine)

Analysis for C$_{23}$H$_{21}$N$_9$O$_6$S$_2$.3HCl.3H$_2$O: Calculated: C 36.98, H 4.05, N 16.88, Cl 14.24; Found: C 36.62, H 3.75, N 16.77, Cl 14.06

Example 9

Using procedures analogous to that described in Example 4, 7β-(2-(2-aminothiazol-4-yl)-2-((5-methylimidazol-4-yl)methoxyimino)acetamido)-3-(1-pyridino)methyl-3-cephem-4-carboxylate trihydrochloride (syn isomer) was obtained.

Analysis for C$_{23}$H$_{22}$N$_8$O$_5$S$_2$.3HCl.3H$_2$O: Calculated: C 38.47, H 3.93, N 15.61; Found: C 38.67, H 4.27, N 15.41

IR: 3400, 1780, 1630

FT-NMR (D$_2$O, δ, ppm, 200 MHz): 2.36 (3H, s, C$_5$—CH$_3$ of imidazole), 3.25 (1H, d, J=18 Hz, C$_2$—H), 3.70 (1H, d, J=18 Hz, C$_2$—H), 5.30 (1H, d, J=5 Hz, C$_6$—H), 5.36 (2H, s, =N—OCH$_2$), 5.42 (1H, d, J=14 Hz,

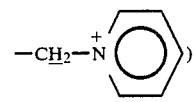

5.66 (1H, d, J=14 Hz,

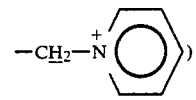

5.88 (1H, d, J=5 Hz, C$_7$—H) 7.21 (1H, s, C$_5$—H of thiazole) 8.16 (2H, t, J=7 Hz, C$_3$ and C$_5$—H of pyridine) 8.61 (1H, s, C$_2$—H of imidazole) 8.64 (1H, t, J=7 Hz C$_4$—H of pyridine) 9.00 (2H, d, J=7 Hz, C$_2$ and C$_6$—H of pyridine)

Example 10

Using procedures analogous to that described in Example 8, 7β-(2-(2-aminothiazol-4-yl)-2-((imidazol-4-yl)methoxyimino)acetamido)-3-(4-methyl-1-pyridinio)-methyl-3-cephem-4-carboxylate trihydrochloride (syn isomer) was obtained.

Analysis for C$_{23}$H$_{22}$N$_8$O$_5$S$_2$.3HCl.3H$_2$O: Calculated: C 38.47, H 3.93, N 15.61; Found: C 38.01, H 3.82, N 14.52

IR: 3400, 1770, 1600, 1520

FT-NMR (D$_2$O, δ, ppm, 200 MHz): 2.66 (3H, s, C$_4$—CH$_3$ of pyridine), 3.26 (1H, d, J=18 Hz, C$_2$—H), 3.68 (1H, d, J=18 Hz, C$_2$—H), 5.30 (1H, d, J=5 Hz, C$_6$—H), 5.36 (1H, d, J=14 Hz,

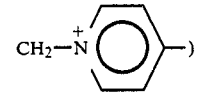

5.41 (2H, s, =N—OCH$_2$), 5.58 (1H, d, J=14 Hz,

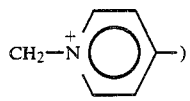)

5.85 (1H, d, J=5 Hz, C$_7$—H), 7.22 (1H, s, C$_5$—H of thiazole), 7.64 (1H, s, C$_4$—H of imidazole), 7.94 (2H, d, J=7 Hz, C$_3$ and C$_5$—H of pyridine), 8.76 (3H, C$_2$ and C$_6$—H of pyridine, C$_2$—H of idazole)

Example 11

5.23 g of 2-(2-tritylaminothiazol-4-yl)-2-((1-methylimidazol-5-yl)methoxyimino)acetic acid and 3.28 g of tertiary butyl 7β-amino-3-acetoxymethyl-3-cephem-4-carboxylate were suspended in 200 ml of methylene chloride and 1.35 g of 1-hydroxybenzotriazole was added thereto. A mixture of 2.27 g of DCC and 20 ml of methylene chloride was added to the mixture under stirring and cooling in an ice-bath. The resulting mixture was stirred for 1 hour at the same temperature and then stirred for 23 hours at room temperature. The insoluble material was removed by filtration and the filtrate was concentrated to dryness in vacuo. The residue was purified by silica gel column chromatography with a 1% methanol-chloroform eluent to give 6.49 g of tertiary butyl 7β-(2-(2-tritylaminothiazol-4-yl)-2-((1-methylimidazol-5-yl)methoxyimino)acetamido)-3-acetoxymethyl-3-cephem-4-carboxylate (syn isomer) as a powder.

CW-NMR (CDCl$_3$, δ, ppm): 1.55 (9H, s, tertiary butyl), 2.08 (3H, s, CH$_3$CO), 3.20, 3.50 (each 1H, each d, J=18 Hz, C$_2$—H), 3.63 (3H, s, CH$_3$—N), 5.22 (2H, s, CH$_2$O—N=), 5.85–6.00 (1H, m, C$_7$—H), 6.83 (1H, s, C$_5$—H of thiazole), 6.92 (1H, s, C$_4$—H of imidazole), 7.07 (1H, s, C$_2$—H of imidazole), 7.30 (15H, s, trityl), 8.51 (1H, d, J=8 Hz, —CONH—)

6.49 g of the above product was dissolved in a mixture of 80 ml of trifluoroacetic acid and 5 ml of anisole under cooling in an ice-bath and the mixture was stirred for 2 hours at the same temperature. Trifluoroacetic acid was distilled off in vacuo and then 80 ml of formic acid and 5 ml of concentrated hydrochloric acid were added to the residue. The mixture was stirred for one hour under cooling in an ice-bath and stirred for 30 minutes at room temperature. The reaction mixture was cooled in an ice-bath and acetone was added thereto for dissolving the insoluble material and then ether was added to the mixture. The precipitate formed was collected by filtration and washed with ether and dried in vacuo. The precipitate was purified by column chromatography using 300 ml of HP-20 as a support with a 2% aqueous solution of THF eluent to give 1.65 g of 7β-(2-(2-aminothiazol-4-yl)-2-((1-methylimidazol-5-yl)methoxyimino)acetamido)-3-acetoxymethyl-3-cephem-4-carboxylic acid (syn isomer).

CW-NMR (D$_2$O, δ, ppm): 2.12 (3H, s, CH$_3$CO), 3.50 (2H, m, C$_2$—H), 5.10–5.55 (3H, m, —CH$_2$—OAc and C$_6$—H), 5.35 (2H, s, CH$_2$O—N=), 5.78 (1H, d, J=5 Hz, C$_7$—H), 7.00 (1H, s, C$_5$—H of thiazole), 7.61 (1H, s, C$_4$—H of imidazole), 8.71 (1H, s, C$_2$—H of imidazole)

A mixture of 450 mg of the above product, 1 ml of pyridine, 1 ml of water and 3 g of sodium iodide was stirred for 2 hours on a water bath heated to 70°–80° C. The reaction mixture cooled to room temperature was added to 100 ml of acetone. The precipitate formed was collected by filtration and washed with acetone and then purified by column chromatography using 40 ml of HP-20 as a support with a 3% aqueous solution of THF eluent and HPLC using Partisil as a support with water eluent (adjusted to pH 2–3 with hydrochloric acid) to give 7β-(2-(2-aminothiazol-4-yl)-2-((1-methylimidazol-5-yl)methoxyimino)acetamido)-3-(1-pyridinio)methyl-3-cephem-4-carboxylate trihydrochloride (syn isomer).

Analysis for C$_{23}$H$_{22}$N$_8$O$_5$S$_2$.3HCl.3H$_2$O: Calculated: C 38.47, H 4.35, N 15.61; Found: C 38.39, H 4.33, N 15.78

FT-NMR (D$_2$O, δ, ppm, 200 MHz): 3.23, 3.67 (each 1H, each d, J=18 Hz, C$_2$—H), 3.90 (3H, s, CH$_3$—N), 5.44 (2H, s, CH$_2$ON=), 5.42, 5.63 (each 1H, each d, J=15 Hz, —CH$_2$OAc), 5.87 (1H, d, J=5 Hz, C$_7$—H), 7.20 (1H, s, C$_5$—H of thiazole), 7.65 (1H, s, C$_4$—H of imidazole), 8.14 (2H, t, J=7 Hz, C$_3$ and C$_5$—H of pyridine), 8.63 (1H, t, J=7 Hz, C$_4$—H of pyridine), 8.76 (1H, d, C$_2$—H of imidazole), 8.97 (2H, d, J=7 Hz, C$_2$ and C$_6$—H of pyridine)

Example 12

Using procedures analogous to that described in Example 8, 7β-(2-(2-aminothiazol-4-yl)-2-((2-methylimidazol-4-yl)methoxyimino)acetamido)-3-(1-pyridinio)methyl-3-cephem-4-carboxylate trihydrochloride (syn isomer) was obtained.

Analysis for C$_{23}$H$_{22}$N$_8$O$_5$S$_2$.3HCl.5/2H$_2$O: Calculated C 38.96, H 4.26, N 15.80; Found C 39.14, H 4.35, N 14.90

IR: 1780, 1630

FT-NMR (D$_2$O, δ, ppm, 200 MHz): 2.60 (3H, s, C$_2$—CH$_3$ of imidazole), 3.28 (1H, d, J=18 Hz, C$_2$—H), 3.73 (1H, d, J=18 Hz, C$_2$—H), 5.30 (1H, d, J=5 Hz, C$_6$—H), 5.32 (2H, s, =N—OCH$_2$), 5.42 (1H, d, J=14 Hz,

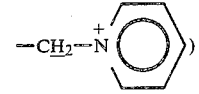)

5.66 (1H, d, J=14 Hz,

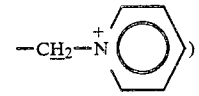)

5.90 (1H, d, J=5 Hz, C$_7$—H), 7.21 (1H, s, C$_5$—H of thiazole), 7.44 (1H, s, C$_5$—H of imidazole), 8.16 (2H, t, J=7 Hz, C$_3$ and C$_5$—H of pyridine), 8.64 (1H, t, J=7 Hz, C$_4$—H of pyridine), 9.00 (2H, d, J=7 Hz, C$_2$ and C$_6$—H)

Example 13

Using procedures analogous to that described in Example 8, 7β-(2-(2-aminothiazol-4-yl)-2-((imidazol-4-yl)methoxyimino)acetamido)-3-(3-carbamoyl-1-pyridinio)methyl-3-cephem-4-carboxylate trihydrochloride (syn isomer) was obtained.

IR: 1780

FT-NMR (D$_2$O, δ, ppm, 200 MHz): 3.32 (1H, d, J=18 Hz, C$_2$—H), 3.76 (1H, d, J=18 Hz, C$_2$—H), 5.36 (1H, d, J=5 Hz, C$_6$—H), 5.42 (2H, s, =N—OCH$_2$), 5.50 (1H, d, J=16 Hz,

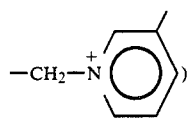

5.82 (1H, d, J=16 Hz,

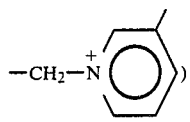

5.92 (1H, d, J=5 Hz, C$_7$—H) 7.24 (1H, s, C$_5$—H of thiazole) 7.65 (1H, s, C$_5$—H of imidazole) 8.30 (1H, t, J=6 Hz, C$_5$—H of pyridine) 8.78 (1H, s, C$_2$—H of imidazole) 9.02 (1H, d, J=6 Hz, C$_6$—H of pyridine) 9.20 (1H, d, J=6 Hz, C$_4$—H of pyridine) 9.46 (1H, s, C$_2$—H of pyridine)

Analysis for C$_{23}$H$_{21}$N$_9$O$_6$S$_2$.3HCl.3H$_2$O: Calculated: C 36.98, H 4.05, N 16.87; Found: C 37.01, H 3.97, N 16.78

Example 14

3.08 ml of DMF and 3.64 ml of phosphorus oxychloride were added dropwise to 30 ml of methylene chloride under cooling in an ice-bath. The mixture was added to a mixture of 16.23 g of 2-(2-tritylaminothiazol-4-yl)-2-((N-tritylimidazol-4-yl)methoxyimino)acetic acid and 120 ml of methylene chloride under cooling to −15° C. and the resulting mixture was stirred for one hour. N,O-Bis(trimethylsilyl)acetamide was added to a mixture of 120 ml of acetonitrile and 15.1 g of 7β-amino-3-(1-pyridinio)methyl-3-cephem-4-carboxylate dihydrochloride until the insoluble material dissolved. The above reaction mixture was added to the resulting mixture cooled in an ice-bath and after 20 minutes the temperature of the resulting mixture was raised to room temperature, followed by stirring for 1.5 hours. Water was added to the reaction mixture. The organic solvent layer was washed with water and SSC and dried with sodium sulfate and then concentrated to dryness to give 22.8 g of the product in the form of light brown powder.

A mixture of 200 ml of 98% formic acid and 10 ml of concentrated hydrochloric acid was cooled in an ice-bath and 22.8 g of the above product was added thereto. The resulting mixture was stirred and after 15 minutes the temperature was raised to room temperature and then the mixture was stirred for one hour. The precipitated triphenylcarbinol was removed by filtration and the filtrate was concentrated to dryness. The residue was purified by column chromatography using HP-20 as a support with water and a 5% aqueous solution of THF eluent and HPLC using Partisil as asupport with water eluent (adjusted to pH 2-3 with hydrochloric acid) to give 7β-(2-(2-aminothiazol-4-yl)-2-((imidazol-4-yl)methoxyimino)acetamido)-3-(1-pyridinio)methyl-3-cephem-4-carboxylate trihydrocloride (syn isomer).

The NMR data of the product was identical with those of the compound obtained at Example 1.

IR: 1780, 1630

Analysis for C$_{22}$H$_{20}$N$_8$O$_5$S$_2$.3HCl.3H$_2$O: Calculated: C 37.53, H 4.15, N 15.92; Found: C 37.18, H 4.29, N 15.46

Example 15

306 mg of 1-hydroxybenzotriazole and 412 mg of DCC were added to 20 ml of a mixture of DMF and 1.5 g of 2-(2-tritylaminothiazol-4-yl)-2-((N-tritylimidazol-4-yl)methoxyimino)acetic acid and the resulting mixture was stirred for 3 hours at room temperature. The insoluble material was removed by filtration and a mixture of DMF, 544 mg of 7β-amino-3-acetoxymethyl-3-cephem-4-carboxylic acid and 404 mg of triethylamine was added to the filtrate and then the resulting mixture was stirred overnight. The solvent was distilled off and ethyl acetate was added to the residue. The mixture was washed with water and dried with sodium sulfate and then concentrated to dryness. Ether was added to the residue and the precipitate formed was collected by filtration to give 1.44 g of the product as a powder.

The product was dissolved in 50 ml of formic acid and 2 ml of concentrated hydrochloric acid was added thereto and then the resulting mixture was stirred for 2 hours at room temperature. The reaction mixture was concentrated to dryness and acetone was added to the residue. The precipitate formed was collected by filtration and purified by column chromatography using 200 ml of HP-20 as a support with a 5% aqueous solution of THF eluent and HPLC using Partisil as a support with water eluent (adjusted to pH 2-3 with hydrochloric acid) to give 7β-(2-(2-aminothiazol-4-yl)-2-((imidazol-4-yl)methoxyimino)acetamido)-3-acetoxymethyl-3-cephem-4-carboxylic acid dihydrochloride (syn isomer).

FT-NMR (D$_2$O, β, ppm, 200 MHz): 2.12 (3H, s, CH$_3$CO), 3.46, 3.75 (each 1H, each d, J=18 Hz C$_2$—H), 5.25 (1H, d, J=5 Hz, C$_6$—H), 5.44 (2H, s, CH$_2$ON=), 5.86 (1H, d, J=5 Hz, C$_7$—H), 7.25 (1H, s, C$_5$—H of thiazol), 7.66 (1H, s, C$_4$—H of imidazole), 8.80 (1H, s, C$_2$—H of imidazole)

Analysis for C$_{19}$H$_{19}$N$_7$O$_7$S$_2$.2HCl.3H$_2$O: Calculated: C 35.19, H 4.20, N 15.12; Found: C 34.85, H 4.15, N 15.14

A mixture of 650 mg of the above product, 1.5 ml of water, 168 mg of sodium bicarbonate, 1.5 ml of pyridine and 3 g of sodium iodide was stirred for 2 hours in a water-bath heated to 70°-80° C. The reaction mixture was cooled to room temperature and was added to 100 ml of acetone. The precipitate formed was collected by filtration and washed with acetone. The product was purified by column chromatography using 50 ml of HP-20 as a support with 3% aqueous solution of THF eluent and HPLC using Partisil as a support with water eluent (adjusted to pH 2-3 with hydrochloric acid) to give 7β-(2-(2-aminothiazol-4-yl)-2-((imidazol-4-yl)methoxyimino)acetamido)-3-(1-pyridinio)methyl-3-cephem-4-carboxylate trihydrochloride. (syn isomer)

The NMR data of the product was idintical with those of the compound obtained at Example 1.

Analysis for C$_{22}$H$_{20}$N$_8$O$_5$S$_2$.3HCl.3H$_2$O: Calculated: C 37.53, H 4.15, N 15.92; Found: C 37.56, H 4.08, N 15.51

Example 16

1.05 g of 2-(2-tritylaminothiazol-4-yl)-2-((1-methylpyrazol-3-yl)methoxyimino)acetic acid was dissolved in 30 ml of methylene chloride and 270 mg of 1-hydroxybenzotriazole and 412 mg of DCC were added thereto. The mixture was stirred for 3 hours at room temperature. A mixture of 544 mg of 7β-amino-3-acetoxymethyl-3-cephem-4-carboxylic acid, 0.8 ml of triethylamine and 30 ml of methylene chloride was added thereto.

The resulting mixture was stirred overnight at room temperature. The insoluble material was removed by filtration and the filtrate was washed with a 10% aqueous solution of citric acid, water and SSC and then dried with sodium sulfate. The solvent was distilled off and the residue was treated with ether to give 1.5 g of the product as a yellow powder. 10 ml of formic acid and 6 ml of concentrated hydrochloric acid were added to the product under cooling in an ice-bath. The resulting mixture was stirred for 2 hours at room temperature and the reaction mixture was concentrated to dryness. Ether was added to the residue. The precipitate formed was collected by filtration and washed with ether and then dried to give 810 mg of 7β-(2-(2-aminothiazol-4-yl)-2-((1-methylpyrazol-3-yl)methoxyimino)acetamido)-3-acetoxymethyl-3-cephem-4-carboxylic acid dihydrochloride (syn isomer).

CW-NMR (D$_2$O, δppm): 2.25 (3H, s, OCOCH$_3$), 3.95 (3H, s, N—CH$_3$), 5.15 (1H, d, J=4 Hz, C$_6$—H), 5.30 (2H, s, CH$_2$O), 5.76 (1H, d, J=4 Hz, C$_7$—H), 6.52 (1H, d, J=1.5 Hz, C$_4$—H of pyrazole), 7.12 (1H, s, C$_5$—H of thiazole), 7.70 (1H, d, J=1.5 Hz, C$_5$—H of pyrazole)

A mixture of 600 mg of the above product, 2 g of sodium iodide, 0.5 ml of water and 0.5 ml of pyridine was heated for 2 hours at 75° C. under nitrogen gas. 400 ml of acetone was added dropwise to the reaction mixture. The insoluble material was collected by filtration and washed with acetone and then purified by column chromatography using HP-20 as a support with 5% aqueous solution of THF eluent and HPLC using Partisil as a support with 15% aqueous solution of methanol eluent to give 25 mg of 7β-(2-(2-aminothiazol-4-yl)-2-((1-methylpyrazol-3-yl)methoxyimino)acetamido)-3-(1-pyridinio)methyl-3-cephem-4-carboxylate (syn isomer).

FT-NMR (D$_2$O, δppm): 3.16, 3,64 (2H, AB-q, J=17 Hz, C$_2$—H), 3.82 (3H, s, NCH$_3$), 5.20 (2H, s, CH$_2$O), 5.25 (1H, d, J=5 Hz, C$_6$—H), 5.38, 5.60 (2H, AB-q, J=14 Hz,

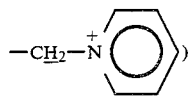

5.86 (1H, d, J=5 Hz, C$_7$—H), 6.42 (1H, s, C$_4$—H of pyrazole), 7.02 (1H, s, C$_5$—H of thiazole), 7.55 (1H, s, C$_5$—H of pyrazole), 8.14 (2H, t, J=7 Hz, C$_3$ and C$_5$—H of pyridine), 8.62 (1H, t, J=7 Hz, C$_4$—H of pyridine), 8.99 (2H, d, J=7 Hz, C$_2$ and C$_6$—H of pyridine)

Example 17

0.14 ml of triethylamine and 268 mg of phenyl N-phenylphosphoramidochloridate were added to a mixture of 20 ml of methylene chloride and 523 g of 2-(2-tritylaminothiazol-4-yl)-2-((1-methylpyrazol-5-yl)methoxyimino)acetic acid, followed by stirring for 3 hours at room temperature. A mixture of 450 mg of 7β-amino-3-(1-pyridiniomethyl)-3-cephem-4-carboxylate hydrochloride, 0.75 ml of N,O-bis(trimethylsilyl)acetamide and 30 ml of methylene chloride was added dropwise thereto. The resulting mixture was stirred for 15 hours at room temperature. The reaction mixture was washed with water and SSC and then dried with sodium sulfate. The solvent was distilled off to give 900 mg of the product as a yellow powder. 10 ml of formic acid and 1 ml of concentrated hydrochloric acid were added to the product and the resulting mixture was stirred for 1.5 hours at room temperature. Acetone was added to the reaction mixture under cooling in an ice-bath for dissolving the insoluble material and ether was added thereto. The precipitate formed was collected by filtration and washed with ether to give 500 mg of the product as a yellow powder. The product was purified by column chromatography using HP-20 as a support with a 3% aqueous solution of THF eluent and HPLC using Particil as a support with a 15% aqueous solution of methanol eluent to give 30 mg of 7β-(2-(2-aminothiazol-4-yl)-2-((1-methylpyrazol-5-yl-methoxyimino)acetamido)3-(1-pyridinio)methyl-3-cephem-4-carboxylate (syn isomer).

FT-NMR (D$_2$O, δ,ppm): 3.00, 3.56 (2H, AB-q, J=17 Hz, C$_2$—H), 3.83 (3H, s, NCH$_3$), 5.11 (1H,d, J=5 Hz, C$_6$—H), 5.31 (2H, s, CH$_2$O), 5.36, 5.58 (2H, ABq, J=16 Hz,

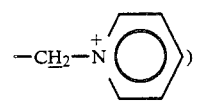

5.79 (2H, d, J=5 Hz, C$_7$—H), 6.43 (1H, s, C$_4$—H of pyrazole), 7.04 (1H, s, C$_5$—H of thiazole), 7.38 (1H, s, C$_3$—H of pyrazole), 8.15 (2H, t, J=7 Hz, C$_3$ and C$_5$—H of pyridine). 8.64 (1H, t, J=7 Hz, C$_4$—H of pyridine), 8.99 (2H, d, J=7 Hz, C$_2$ and C$_6$—H of pyridine)

Example 18

2.26 g of 2-(2-tritylaminothiazol-4-yl)-2-((N-trityl-1,2,3-triazol-4-yl)methoxyimino)acetic acid was dissolved in 90 ml of methylene chloride and 0.62 g of DCC, 0.41 g of N-hydroxybenzotriazole and 0.98 g of tertiary butyl 7β-amino-3-acetoxymethyl-3-cephem-4-carboxylate were added thereto under stirring at room temperature. The resulting mixture was stirred for 2 hours at room temperature. The insoluble material was removed by filtration and the filtrate was concentrated to dryness. The oily residue was purified by silica gel column chromatography with a chloroform eluent to give 2.40 g of the product as a form. The product was dissolved in 3 ml of anisole and 24 ml of trifluoroacetic acid was added thereto under stirring and cooling in an ice-bath. The resulting mixture was stirred for 1.5 hours at room temperature and then concentrated to dryness in vacuo. 25 ml of formic acid was added to the residue and the mixture was stirred for one hour at room temperature and the reaction mixture was concentrated to dryness. Ether was added to the residue and the precipitate formed was collected by filtration and washed with ether and dried in vacuo to give 0.88 g of crude product as a powder. 0.2 g of the crude product was dissolved in a 5% aqueous solution of sodium bicarbonate and purified by HPLC using Partisis as a support with 2% aqueous solution of methanol eluent to give sodium 7β-(2-(2-aminothiazol-4-yl)-2-((1,2,3-triazol-4-yl)methoxyimino)acetamido)-3-acetoxymethyl-3-cephem-4-carboxylate (syn isomer).

IR: 3650-2600, 1760, 1655, 1600

FT-NMR (D$_2$O, δ,ppm): 2.10 (3H, s, —COCH$_3$), 3.32 (1H, d, J=18 Hz, C$_2$—H), 3.64 (1H, d, J=18 Hz, C$_2$—H), 5.17 (1H, d, J=5 Hz, C$_6$—H), 5.41 (2H, s, OCH$_2$), 5.80 (1H, d, J=7 Hz, C$_7$—H), 7.06 (1H, s, C$_5$—H of thiazole), 8.04 (1H, s, C$_5$—H of triazole)

633 mg of the above crude product was dissolved in a mixture of 0.45 ml of pyridine, 93 mg of sodium bicarbonate and 0.75 ml of water and then 2.34 g of sodium iodide was added thereto. The resulting mixture was stirred for 1.5 hours under nitrogen gas in a bath heated to 70°–75° C. After cooling, acetone was added to the reaction mixture. The precipitate formed was collected by filtration and washed with acetone and then dried in vacuo to give 470 mg of the product as a powder. The product was purified by column chromatography using 80 ml of HP-20 as a support with 5% aqueous solution of THF and 20% aqueous solution of THF eluent and HPLC using Bondapak as a support with 7.5% aqueous solution of methanol eluent to give 7β-(2-(2-amino-thiazol-4-yl)-2-((1,2,3-triazol-4-yl)methox-yimino)acetamido)-3-(1-pyridinio)methyl-3-cephem-4-carboxylate (syn isomer).

Analysis for $C_{21}H_{19}N_9O_5S_2.3H_2O$: Calculated: C 42.34, H 4.23, N 21.17; Found: C 42.38, H 3.80, N 21.08
IR: 3600–2500, 1770, 1610
FT-NMR ($D_2O$, δ,ppm): 3.13 (1H, d, J=18 Hz, $C_2$—H), 3.60 (1H, d, J=18 Hz, $C_2$—H), 5.23 (1H, d, J=5 Hz, $C_6$—H), 5.38 (1H, d, J=14 Hz,

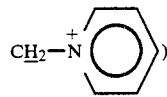

5.39 (2H, s, $OCH_2$), 5.58 (1H, d, J=14 Hz,

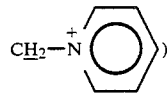

5.84 (1H, d, J=5 Hz, $C_7$—H), 7.04 (1H, s, $C_5$—H of thiazole), 8.02 (1H, s, $C_5$—H of triazole), 8.13 (2H, t, J=7 Hz, $C_3$ and $C_5$—H of pyridine), 8.63 (1H, t, J=7 Hz, $C_4$—H of pyridine), 8.98 (2H, d, J=7 Hz, $C_2$ and $C_6$—H of pyridine)

Example 19

2.19 g of tertiary butyl 7β-(2-(2-tritylaminothiazol-4-yl)-2-((N-tritylimidazol-4-yl)methox-yimino)acetamido)-3-bromomethyl-3-cephem-4-carboxylate 1-oxide (syn isomer) obtained as intermediate in Example 8 was dissolved in 100 ml of methylene chloride and 1.44 ml of pyridazine was added thereto. The resulting mixture was stirred for 16 hours at room temperature. The reaction mixture was concentrated to a half volume and 200 ml of ether was added thereto. The precipitate formed was collected by filtration and recrystallized several times from chloroform-ether to give 1.73 g of the product as a powder. The product was dissolved in 14 ml of DMF and the mixture was cooled to −60° C. and then 0.26 ml of phosphorus trichloride was added dropwise thereto. The resulting mixture was stirred for 1.5 hours at −50° to −45° C. and cooled to −60° C. Ethyl acetate was added to the reaction mixture and the mixture was washed with water and SSC and dried with sodium sulfate and then concentrated to dryness to give 1.05 g of the product as a powder. The product was added to 1.57 ml of anisole and 11 ml of trifluoroacetic acid was added thereto and the resulting mixture was stirred for 1.5 hours at room temperature. The solvent was distilled off and 10 ml of 98% formic acid was added to the residue and 0.65 ml of concentrated hydrochloric acid was added thereto under cooling in an ice-bath. The resulting mixture was stirred for 30 minutes at room temperature. Ether and acetone were added to the reaction mixture and the precipitate formed was collected by filtraiton to give 551 mg of the product as a powder. The product was purified by column chromatography using HP-20 as a support with water and 2% aqueous solution of THF eluent and HPLC using Partisil as a support with water eluent (adjusted to pH 2–3 with hydrochloric acid) to give 7β-(2-(2-aminothiazol-4-yl)-2-((imidazol-4-yl)methoxyimino)acetamido)-3-(1-pyridazinio)methyl-3-cephem-4-carboxylate trihydrochloride (syn isomer).

IR: 1780, 1630
FT-NMR ($D_2O$, δ, ppm 200 MHz): 3.62 (1H, d, J=18 Hz, $C_2$—H), 3.82 (1H, d, J=18 Hz, $C_2$—H), 5.30 (1H, d, J=5 Hz, $C_6$—H), 5.42 (2H, s, =N—$OCH_2$), 5.74 (1H, d, J=14 Hz,

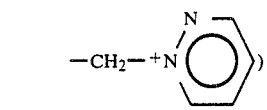

5.86 (1H, d, J=14 Hz,

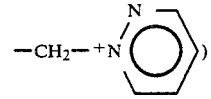

5.88 (1H, d, J=5 Hz, $C_7$—H), 7.22 (1H, s, $C_5$—H of thiazole), 7.65 (1H, s, $C_5$—H of imidazole), 8.62 (2H, s, t, J=7 Hz, $C_4$ and $C_5$—H of pyridazine), 8.78 (1H, s, $C_2$—H of imidazole), 9.56 (1H, d, J=7 Hz, $C_3$—H of pyridazine), 9.88 (1H, d, J=7 Hz, $C_6$—H of pyridazine)

Analysis for $C_{21}H_{19}N_9O_5S_2.3HCl.4H_2O$: Calculated: C 34.88, H 4.18, N 17.43; Found: C 34.52, H 3.89, N 17.06

Example 20

1.5 g of 2-(2-tritylaminothiazol-4-yl)-2-((N-tritylimidazol-4-yl)methoxyimino)acetic acid, 306 mg of 1-hydroxy-benzotriazole and 412 mg of DCC were added to methylene chloride and the resulting mixture was stirred for 3 hours at room temperature. The insoluble material was removed by filtration and a mixture of DMF, 544 mg of 7β-amino-3-acetoxymethyl-3-cephem-4-carboxylic acid and 404 mg of triethylamine was added to the filtrate and the resulting mixture was stirred overnight. The solvent was distilled off and ethyl acetate was added to the residue. The mixture was washed with water and dried with sodium sulfate and then concentrated to dryness. Ether was added to the residue and the precipitate formed was collected by filtration to give 1.44 g of a powdery product. The product was dissolved in 50 ml of formic acid and 2 ml of concentrated hydrochoric acid was added thereto. The resulting mixture was stirred for 2 hours at room temperature. The reaction mixture was concentrated to dryness and acetone was added to the residue. The precipitate formed was collected by filtration and purified by column chromatography using 200 ml of HP-20 as a support with 5% aqueous solution of THF eluent and HPLC using 200 ml of Partisil as a support with water eluent (adjusted to pH 2–3 with hydrochloric acid) to give 7β-(2-(2-aminothiazol-4-yl)-2-((imidazol-4-yl)methoxyimino)acetamido)-3-acetoxymethyl-3-cephem-4-carboxylic acid dihydrochloride (syn isomer).

FT-NMR (D₂O, δ, ppm, 200 MHz): 2.12 (3H, s, CH₃CO), 3.46, 3.75 (each 1H, each d, J=18 Hz, C₂—H), 5.25 (1H, d, J=5 Hz, C₆—H), 5.44 (2H, s, —CH₂ON=), 5.86 (1H, d, J=5 Hz, C₇—H), 7.25 (1H, s, C₅—H of thiazole), 7.66 (1H, s, C₄—H of imidazole), 8.80 (1H, s, C₂—H of imidazole)

Analysis for C₁₉H₁₉N₇O₇S₂.2HCl.3H₂O: Calculated: C 35.19, H 4.20, N 15.12; Found: C 34.85, H 4.15, N 15.14

What we claim is:
1. 7β-(2-(2-aminothiazol-4-yl)-2-((imidazol-4-yl)methoxyimino)acetamido)-3-(1-pyridinio)methyl-3-cephem-4-carboxylate and a physiologically acceptable salt thereof.

* * * * *